United States Patent
Bundock et al.

(10) Patent No.: US 10,995,338 B2
(45) Date of Patent: May 4, 2021

(54) METHOD FOR REMOVING GENETIC LINKAGE IN A PLANT

(71) Applicant: KEYGENE N.V., Wageningen (NL)

(72) Inventors: Paul Bundock, Wageningen (NL); Jeroen Stuurman, Wageningen (NL)

(73) Assignee: KEYGENE N.V., Wageningen (NL)

( * ) Notice: Subject to any disclaimer, the term of this patent is extended or adjusted under 35 U.S.C. 154(b) by 252 days.

(21) Appl. No.: 14/655,633

(22) PCT Filed: Dec. 20, 2013

(86) PCT No.: PCT/NL2013/050939
§ 371 (c)(1),
(2) Date: Jun. 25, 2015

(87) PCT Pub. No.: WO2014/104878
PCT Pub. Date: Jul. 3, 2014

(65) Prior Publication Data
US 2015/0351340 A1      Dec. 10, 2015

Related U.S. Application Data

(60) Provisional application No. 61/746,399, filed on Dec. 27, 2012.

(51) Int. Cl.
| | | |
|---|---|---|
| *C12N 15/82* | (2006.01) | |
| *A01H 1/04* | (2006.01) | |
| *C12N 9/22* | (2006.01) | |

(52) U.S. Cl.
CPC .......... *C12N 15/8213* (2013.01); *A01H 1/04* (2013.01); *C12N 9/22* (2013.01); *C12N 15/8241* (2013.01); *C07K 2319/81* (2013.01)

(58) Field of Classification Search
None
See application file for complete search history.

(56) References Cited

U.S. PATENT DOCUMENTS

| | | | | |
|---|---|---|---|---|
| 8,106,255 B2 * | 1/2012 | Carroll | ............... | A01K 67/0339 435/468 |
| 2004/0023388 A1 * | 2/2004 | Rozwadowski | ... | C12N 15/8213 435/455 |
| 2011/0203012 A1 * | 8/2011 | Dotson | .............. | C12N 15/8257 800/278 |
| 2012/0196370 A1 | 8/2012 | Urnov et al. | | |

FOREIGN PATENT DOCUMENTS

| | | |
|---|---|---|
| EP | 0 270 120 A2 | 6/1988 |
| EP | 2 316 954 A1 | 5/2011 |
| WO | WO-00/54574 | 9/2000 |
| WO | WO-03/104451 A2 | 12/2003 |
| WO | WO 2007/030014 A2 | 3/2007 |
| WO | WO 2011/078665 A1 | 6/2011 |

OTHER PUBLICATIONS de Pater et al. ZFN-induced mutagenesis and gene-targeting in *Arabidopsis* through Agrobacterium-mediated floral dip transformation. Plant Biotechnol J. Oct. 2009;7(8):821-35.*
Pacher et al. Two unlinked double-strand breaks can induce reciprocal exchanges in plant genomes via homologous recombination and nonhomologous end joining. Genetics. Jan. 2007;175(1):21-9. Epub Oct. 22, 2006.*
International Search Report and Written Opinion of the International Searching Authority issued in Netherlands Application No. NL2010061 dated Aug. 15, 2013.
Brunet, et al. "Chromosomal translocations induced at specified loci in human stem cells", PNAS (Jun. 30, 2009) vol. 106, No. 26, pp. 10620-10625.
Canady, et al. "Homeologous Recombination in *Solanum lycopersicoides* Introgression Lines of Cultivated Tomato", Genetics (Dec. 2006) vol. 174, pp. 1775-1788.
International Search Report in PCT/NL2013/050939 dated Apr. 8, 2014.
Simsek, et al. "DNA Ligase III Promotes Alternative Nonhomologous End-Joining during Chromosomal Translocation Formation", PLoS Genetics (Jun. 2011), vol. 7, Issue 6, pp. 1-11.
Office Action issued in co-pending Japanese Application No. P2015-550353 dated Nov. 14, 2017.

\* cited by examiner

*Primary Examiner* — Cynthia E Collins
(74) *Attorney, Agent, or Firm* — Foley & Lardner LLP; Sunit Talapatra

(57) ABSTRACT

The current disclosure relates to the field of plants, in particular to the fields of plant breeding and plant genetics. More particular, the disclosure concerns inventive methodology that may be useful in improving plant properties. In particular the invention may be useful in removing linkage drag. Also provided are plant and plant parts obtained with the method disclosed herein.

12 Claims, 7 Drawing Sheets

Specification includes a Sequence Listing.

*Figure 2*

```
CCTCAACAACAATGGCGGCTGCATCTCCATCTCCTTGTTTTTCCAAAACCCTACCTCCATCTTCATCAAA
ATCTTCCACCCTTCTTCCCAAATCTACCTTTACTTTCCACAATCACCCTAAAAAAGCATCACCCCTTCAC
CTTACACACACCCAACATCATAGCCGTTTCACTGTTTCAAATGTCATCCTATCAACCACGACGCATGACG
ACGTTTCTGAACCCGAAATCTTTGTTTCCCGTTTCGCCCCTGACGAACCCAGAAAGGGTTGTGATGTTCT
TGTGGAGGCACTTGAAAGGGAAGGGGTTAAGGATGTGTTTGCATACCCAGGAGGTGCTTCCATGGAGATT
CATCAGGCTTTGACACGTTCAAATATTATTCGTAATGTGC***TGCCACGTC***ATGAAC***AGGGTGGTG***TGTTTG
CTGCAGAGGGTTACGCACGGGCTACTGGGTTCCCTGGTGTTTGTATTGCTACATCTGGTCCGGGAGCTAC
GAATCTTGTTAGCGGTCTTGCTGATGCTTTGTTGGATAGTATCCCGATTGTTGCTATTACCGGTCAAGTG
CCGAGGAGGATGATTGGTACTGATGCGTTTCAGGAAACTCCTATTGTTGAGGTAACGAGATCCATTACGA
AGCATAATTATCTTGTTATGGATGTAGAGGATATTCCTAGGGTTGTTCGTGAAGCGTTTTTTCTAGCGAA
ATCAGGACGGCCTGGACCTGTTTTGATTGATGTTCCTAAGGATATTCAGCAACAATTGGTGATACCTAAT
TGGGATCAGCCAATGAGGTTGCCTGGTTACATGTCTAGGTTGCCTAAATTACCTAATGAGATGCTTTTGG
AACAAATTGTTAGGCTGATTTCAGAGTCAAAGAAGCCTGTTTTGTATGTGGGTGGTGGGTGTTCACAGTC
GAGTGAGGAGCTGAGACGCTTTGTGGAGCTTACGGGTATTCCTGTGGCGAGTACTTTGATGGGTCTTGGA
GCTTTTCCAAGTGGGGATGAGCTTTCTCTTCAAATGTTGGGTATGCATGGGACTGTGTATGCTAATTATG
CGGTGGATAGTAGTGATTTGTTGCTTGCATTTGGGGTGAGGTTTGATGATCGAGTTACTGGTAAATTGGA
AGCTTTTGCTAGCCGAGCTAAGATTGTCCATATTGATATTGATTCGGCTGAGATTGGAAAGAACAAGCAA
CCTCATGTTTCCATCTGTGCAGATATCAAGTTGGCATTACAGGGTTTGAATTCCATATTCGAGAGTAAAA
AAGGTAAGCTGAAGTTGGACTTTTCTGCTTGGAGGCAGGAGTTAACGGAGCAGAAGGTGAAGTACCCATT
GAATTTTAAGACTTTCGGTGAAGCCATCCCTCCCCAATATGCTATTCAGGTTCTTGATGAGTTAACTAAC
GGAAATGCCATCATTAGTACTGGTGTGGGGCAACACCAAATGTGGGCTGCCCAACACTACAAGTACAAAA
AGCCACGCCAATGGCTTACATCTGGTGGATTAGGAGCAATGGGATTTGGTTTGCCTGCTGCTATAGGTGC
GGCTGTTGGAAGACCGGGTGAGATTGTGGTTGATATTGATGGTGATGGGAGTTTTATCATGAATGTGCAG
GAGTTGGCAACAATTAAGGTGGAGAATCTCCCAGTTAAGATTATGTTGCTGAATAATCAACACTTGGGAA
TGGTGGTTCAGTGGGAGGATCGATTCTATAAGGCTAACAGAGCACACACTTACTTGGGTAATCCTGCTAA
TGAGGAAGAGATCTTCCCTAATATGCTGAAATTTGCAGAGGCTTGTGGCGTACCTGCTGCAAGAGTGTCA
CACAGGGATGATCTTAGAGCTGCCATTCAAAAGATGTTAGACACTCCTGGGCCATACTTGTTGGATGTGA
TTGTACCTCATCAGGAGCATGTTCTACCGATGATTCCCAGTGGCGGTGCTTTCAAAGATGTGATTACGGA
GGGTGATGGGAGACGTTCCTATTGACTTTGAGAAGCTACATAACTAGTTCAAGGCATTGTATTATCTAAA
ATAAACTTAATATTTATGTTTACTTAAAAGTTTTTCATTGTGTGAAGGATTTTAGAATTTCTTGTTCTAT
TGGCAGCACCAATTAAGTATTTGGAGCTCTATTTAGTATGACTAAGATTAATTACAAGTGAAGTAGTTAA
GTTCGATAAATCAGCTTTGTTACATTCTATGTTATTTGGTGAACATGAATTCCATTTGGGAGAAGGCTAT
GTCCAGCTTAAGGGCTCAAATTTTTCAGAGAGTGCTGATTCAAAAGGTGAATGCCAAAATCAGATTAGCA
CAAGTTTGCAGAGTTATATTACGCCATCTTTCTGTTTTCAGCTAATTGCTGTTGCAAGGGCTCTACTGAA
GAAGGCCTCTATTTTATTTCTTGATGAGGTAATCTTTGACCCCTTTTGCTCCCCGTGTGTCCGTTGACTT
TTACCATGTATGCTCTGCGTTACAGTTCTGTGGGTGACCTTGGTATCTTCTTATTCACTGTAAATGTTGG
TTTAAGCCTGAATTACCTAGGGGATTCCCCAGGTCGTTTACACAGGGGTTTACATAAGATCAGCTCAGTT
CTCCGGAGAAGTTCTAGCAATCTTGGAGAGCCTATTTCATCTCTGCATGTGAATCTTAGGGCAGTTAATG
```

Figure 2 (continued)

```
CCAAGGATATCAGAGTGAAGATTATAGTGGATGACACCATTTTGCCTTCATCATTAGCAACAACACCTAC
AGAAGATGGAAAAGAGAACGGTGCAGGAAATGGGAAAAGTTTCACAAATGGGGCAAGACGAAGAGAATCC
TTAAAGATGCTGGCAAATCTGTTGGTGGTGGCATAAAGGAAGTGATGTCTGGGAAGTCATCAGGGAAATC
TAAAGAGGAAGTAGAATCATCAGAGACCGAAAGAATGAGCTCTGTGGAATCTGATATTTCTGATGCAGAG
TCTCAACCTTCATCAGTTGATTCACCTCCAGTTGTAGCGCCTTC
```

*Figure 3*

```
ALS2       AATGTGCTGCCACGTCATGAACAGGGTGGTGTGTTTGC
M82(1)     AATGTGCTGCCACGTCA---ACAGGGTGGTGTGTTTGC
M82(2)     AATGTGCTGCCACGTCA----CAGGGTGGTGTGTTTGC
M82(3)     AATGTGCTGCCACGTCA-GAACAGGGTGGTGTGTTTGC
M82(4)     AATGTGCTGCCACGTCATG---AGGGTGGTGTGTTTGC
M82(5)     AATGTGCTGCCACGTC-------GGGTGGTGTGTTTGC
IL7-3(1)   AATGTGCTGCCACGTCA------GGGTGGTGTGTTTGC
IL7-3(2)   AATGTGCTGCCACGTCA---ACAGGGTGGTGTGTTTGC
```

*Figure 4*

```
M82 ALS2         CATCAgGCTTTGACACGTTCaAATATTATTCGTAATGTGCTGCCACGTCATGAACAGGGTGGTG-446bps-TCaGAG
S.pennlii ALS2   CATCAaGCTTTGACACGTTCgAATATTATTCGTAATGTGCTGCCACGTCATGAACAGGGTGGTG-446bps-TCgGAG M82              CATCAgGCTTTGACACGTTCaAATATTATTCGTAATGTGCTGCCACGTCATGAACAGGGTGGTG-446bps-TCaGAG
IL7-3            CATCAaGCTTTGACACGTTCgAATATTATTCGTAATGTGCTGCCACGTCATGAACAGGGTGGTG-446bps-TCgGAG F1               CATCAgGCTTTGACACGTTCaAATATTATTCGTAATGTGCTGCCACGTCATGAACAGGGTGGTG-446bps-TCaGAG
F1               CATCAaGCTTTGACACGTTCgAATATTATTCGTAATGTGCTGCCACGTCATGAACAGGGTGGTG-446bps-TCgGAG F1 x ZFN         CATCAaGCTTTGACACGTTCgAATATTATTCGTAATGTGCTGCCACGTCA------GGGTGGTG-446bps-TCaGAG
F1 x ZFN         CATCAaGCTTTGACACGTTCgAATATTATTCGTAATGTGCTGCCACGTCA-------GGTGGTG-446bps-TCaGAG
F1 x ZFN         CATCAaGCTTTGACACGTTCgAATATTATTCGTAATGTGCTGCCACGTCA------GGGTGGTG-446bps-TCaGAG
F1 x ZFN         CATCAaGCTTTGACACGTTCgAATATTATTCGTAATGTGCTGCCACGTCA---ACAGGGTGGTG-446bps-TCaGAG
F1 x ZFN         CATCAaGCTTTGACACGTTCgAATATTATTCGTAATGTGCTGCCACGTCA----CAGGGTGGTG-446bps-TCaGAG Clone #1         CATCAaGCTTTGACACGTTCgAATATTATTCGTAATGTGCTGCCACGTCA-----AGGGTGGTG-446bps-TCaGAG
Clone #2         CATCAgGCTTTGACACGTTCaAATATTATTCGTAATGTGCTGCCACGTCAT---CAGGGTGGTG-446bps-TCgGAG
```

METHOD FOR REMOVING GENETIC LINKAGE IN A PLANT

CROSS REFERENCE TO RELATED APPLICATIONS

The present application is a National Stage of International Application No. PCT/NL2013/050939 filed on Dec. 20, 2013, which was published on Jul. 3, 2014, as WO 2014/104878 A1, and which claims the benefit of U.S. application Ser. No. 61/746,399 filed Dec. 27, 2012, the entire disclosures of which are incorporated herein by reference.

SEQUENCE LISTING

The instant application contains a Sequence Listing which has been submitted electronically in ASCII format and is hereby incorporated by reference in its entirety. Said ASCII copy, created on Jun. 23, 2017, is named 085342-0600_SL.txt and is 19,635 bytes in size.

FIELD OF THE INVENTION

The current disclosure relates to the field of plants, in particular to the fields of plant breeding and plant genetics. More particular, the disclosure concerns inventive methodology that may be useful in improving plant properties.

PRIOR ART

Recombination results in the new arrangement of genes by various mechanisms such as assortment and segregation, crossing over, gene conversion and transformation. Recombination in plants can occur at numerous stages in plant development. There are two main different classes of recombination in plant cells, homologous recombination (HR) and non-homologous end joining (NHEJ). The HR recombination pathway involves rearrangements between DNA molecules that share the same DNA sequence, whether this is on the same or different chromosomes. This is in contrast with the NHEJ pathway, that is able to generate rearrangements between any DNA molecules, irrespective of any DNA homology between them. The HR pathway is thought to be active in all the different types of plant cell. For instance, HR plays an essential role in gamete formation by promoting crossovers between sister chromatids for correct chromosome segregation and the recombination of different parental alleles (meiotic HR). The HR pathway is also active in mitotic cells where it is mainly involved in the repair of DNA damage at a locus using the sequence information present on the homologous undamaged locus (mitotic HR). This can be present on the same or different chromosome as the damaged locus. The NHEJ pathway is also active in both meiotic and mitotic cells and is very effective at joining non-homologous DNA ends together. One of the main differences between the HR and NHEJ pathways is the fidelity of the process. While HR between related DNA sequences results in recombination in which the DNA sequence of both molecules/loci is preserved the NHEJ pathway often generates small mutations at the position where the recombination occurs, which in itself can be mutagenic.

Plant breeding involves the selection of optimal parental plants which are then crossed and progeny from this cross with improved growth characteristics are selected. Plant breeding has been very successful over the last 100 years in domesticating a wide range of plant species and improving significantly the yield and quality of plant products.

This has been achieved through the selection of allelic variation that provides improvements in both plant cultivation and consumption traits. Typically, a cross is performed between two parent plants to produce the hybrid F1 progeny which are then selfed to create homozygous alleles and the resulting F2 progeny are screened for the phenotype of interest. When plants are crossed to form the hybrid (F1), recombination (crossovers) occur between the different homologous parental plant chromosomes during meiosis, shuffling the genetic information contributed by each parent.

Recombination during meiosis (meiotic HR) is a (semi-)random, homology dependent, process producing male and female gametes that each carry different sets of alleles from the parental plants. If a particular combination of parental loci in the progeny is desired then many individuals must be screened to select those that have inherited the desired parental alleles. Screening can be performed based solely on the phenotype, or as is more often the case, by using molecular markers tightly linked to the allele(s) of interest. This marker assisted breeding (MAB) approach has the advantage that the plants of a F2 population can be screened at an early growth stage so that large populations of mature plants do not need to be maintained and also they can be screened for the presence of many markers linked to multiple alleles. Therefore it is clear that the process of meiotic recombination is the main driver in plant breeding and that processes that affect this can lead to bottlenecks in the breeding process.

The total world population is expected to increase significantly in the coming decades and there is a realization that the yield of many crops must also increase while at the same time utilizing the same area of arable land and using fewer resources such as water and fertilizer. Plant breeding has a large part to play in improving crop yield through the introduction of novel alleles present in the germplasm. However, conventional plant breeding has led to a reduction in the total amount of allelic variation present in cultivated crops, either through conscious selection against traits that were viewed to be deleterious or through unconscious loss of alleles due to the lack of selection pressure on variation that was considered neutral at the time. Due to the reduced allelic variation in cultivated species, the novel alleles that can confer such traits such as novel biotic and abiotic resistances are unlikely to be present in the cultivated germplasm. One likely source of such alleles is in unadapted wild germplasm. Wild germplasm has been extensively used to improve the germplasm of cultivated species when either the growing conditions or the consumer preferences change and the existing gene pool does not have the necessary genetic variation to meet the changing needs. The success of using wild germplasm depends on several factors such as the breadth of variation that can be accessed through crossing (e.g. plant incompatibility, species barriers), the speed at which novel genetic variation can be transferred to address the quickly changing needs and finally how much variation can be transferred from a wild species without the transfer of severe negative effects (linkage drag). Linkage drag may be described as the presence of genetic linkage between two loci, for example one desirable and the other undesirable, on the same chromosome. As a consequence of this genetic linkage the two loci are inherited together during normal meiosis. Unfortunately, with the methods available in the art, removing the genetic linkage between such desired and undesired genes in a plant, and obtaining a plant with only the desired genes and associated traits, has turned out to be difficult, time consuming, and in various cases impossible.

Meiosis is responsible for the formation of reduced gametes (egg cells or pollen) containing half the genetic complement of the parent plant. During meiosis, meiotic recombination occurs between the parental chromosomes resulting in a mixing of parental alleles so that the gametes carry different combinations of parental loci producing different patterns of genetic variation in the progeny plants. Meiotic recombination usually occurs between the euchromatic regions of the parental chromosomes where there is a high degree of synteny, at both the structural and the DNA level. It is well known in the literature that recombination (crossovers) between parental chromosomes is inhibited in regions which are structurally different (such as large deletions, insertions or inversions) or lack DNA sequence identity. This is less of a problem when the parents are derived from a common lineage and are therefore genetically similar but becomes a larger problem when considering crosses with wild germplasm which are likely to be genetically more diverse than the cultivated lines. In such cases the regions at which crossovers can occur between the chromosomes of the wild germplasm and the cultivated germplasm is and inhibited by the aforementioned structural differences in the DNA. When performing a cross between plant lines with cultivated and wild germplasm, F2 plants are selected carrying the desired alleles and then these are backcrossed multiples times with the cultivated plant line, while continuing to select for plants carrying the desired wild germplasm allele(s), to increase the percentage of the genome contributed by the cultivated parent while decreasing the percentage of the genome from the wild parent. In an ideal situation this will result in a plant with the genome of the cultivated parent but carrying a small locus (introgression) from the wild germplasm. As stated before, this backcrossing process is completely dependent on normal meiotic recombination occurring between loci from the two parents. However, due to the presence of structural and sequence differences between the parents meiotic recombination can be suppressed, leading to the presence of large introgressions from the wild germplasm that cannot be made smaller (Canady et al. (2006) Genetics 174, 1775-1788).

As meiotic recombination is suppressed at such regions, subsequent backcrosses are not successful in decreasing the introgression size. This can be a particular problem when both the desired positive trait and also a negative trait are located on the introgression as these cannot be easily separated using meiotic recombination. This explains why there is often linkage drag that cannot be easily broken on introgressions derived from wild germplasm. The approach usually taken to break such linkage drag is to screen many more plants than normal for a recombination event between the two loci. This is sometimes possible, but can be very expensive and has no guarantee of success as the degree of recombination suppression is unknown. There are many examples of introgressions at which no further recombination occurs despite serious efforts to screen very large plant populations. Several publications (e.g. WO03/104451 and WO00/54574) have described methods for enhancing MHR in plants which may increase the chance of obtaining the rare recombination events in regions of suppressed meiotic recombination such as in regions with linkage drag. However, the methods described in these publications propose treatments that enhance the HR pathway between all the homologous loci in the cell which is undesirable in breeding material. In addition, these treatments are also often inherently mutagenic which alter the DNA sequence genome wide and lead to unpredictable phenotypes. For example, the publication EP0270120 teaches that linkage drag can be broken by the growth of plant cells in tissue culture on medium containing high levels of a mutagenic plant growth regulator. As with the other publications the recombination rate genome wide will be affected and thus the plants generated by this method would be unsuitable for further breeding.

Therefore there is a clear need in the art for reproducible and easier methodology allowing the manipulation of the genome of plants, in particular in breeding processes, and in particular allowing the breaking/removing of genetic linkage between two loci on the same chromosome, in particular wherein such loci are both localized in a part of the chromosome were recombination is suppressed.

Problems Solved by the Present Invention

We surprisingly found that the above identified need in the prior art may be solved by using the NHEJ pathway to induce a recombination event specifically only at the introgression with the linkage drag and avoiding altering the recombination or mutation rates throughout the rest of the genome. Indeed, in this invention we disclose a novel use of the NHEJ pathway in plant breeding, specifically for breaking linkage drag. Here we disclose a method which can be applied in somatic plant cells and allows creating a translocation by NHEJ at any specific position between homologous or homeologous chromosomes, for example in a F1 hybrid. The methodology may be used for a wide range of breeding applications, for example for the purpose of elimination of linkage drag, for the purpose of targeted manipulation of polyploid genomes, for the purpose of the production of custom introgressions, for the purpose of simplified fine mapping and for the purpose of generation of gene fusions.

In more detail, the invention involves the introduction of double strand breaks, for example using site specific nucleases (including nuclease systems), into plant cells, including plant protoplasts. The site specific nucleases may be targeted to specific identical sequences at the corresponding position on both homologous chromosomes. These then induce a DNA double strand break on each chromosome which with unexpected high frequency (in approx. 0.8% of cells) are re-joined resulting in an exchange of chromosome arms, which leads to an induced targeted translocation. One additional important advantage of this method is that it only requires tissue culture facilities to identify the desired recombination events rather than screening large plant populations to identify random meiotic HR events, all of which requires a greenhouse. Therefore, use of the method for the purposes given above may also lead to a large cost reduction in the breeding processes itself.

The method according to the invention may, for example, be used for the purpose of:
  a. Breaking linkage drag: Resistance to severe viruses such as TMV and TYCLV have been introduced from wild tomato species and the genes conferring resistance are present on large introgression fragments which are recombinationally silent. There are also genes on these introgressions that negatively affect yield (linkage drag) but cannot be recombined away from the source of resistance. However, this yield loss is accepted as the virus resistance is so valuable. The technique described herein can be used for the purpose of breaking up the introgression fragment at defined positions, thus generating lines with the virus resistance but lacking the linkage drag. All forms of linkage drag are a large problem in breeding and will continue to slow down and complicate plant breeding in the future.

b. Tailored introgressions: Any chromosomal region of known sequence can be linked to any other sequence on the homologous chromosome. This allows one to define the size of the introgression that one would want to have in a final product. In fact, the introgression could comprise a single gene.

c. Fine mapping: Gene mapping uses meiotic recombination to link genes to markers, but is not effective when meiotic recombination is suppressed or when many genes are closely linked. The method disclosed herein, leading to translocation, can be used to divide an introgression fragment into smaller regions which can then be genotyped using markers or be phenotyped. In this way one can quickly identify causal genes.

d. Intra-genic recombination: New sources of resistance are needed as new biotypes of pathogens evolve. Resistance genes are normally present in clusters and recombination between these generates new genes that confer new resistances. However, these are low frequency events and difficult to find. Translocations can be used to combine parts (domains) of resistance genes present in clusters on different chromosomes to create new combinations of domains conferring novel resistances.

e. Homozygosity in polyploidy species: Several polyploidy plant species are allopolyploids, meaning that the separate genomes do not recombine during meiosis. This can be problematic when one of the genomes carries a negative phenotype at a chromosomal position because this cannot be eliminated. Translocations can be induced between the genomes and through selfing a situation can be created whereby whole chromosome arms become completely homozygous. This can also be used to transfer mutations induced in the chromosomes of one genome to the chromosomes of the other genome, which is particularly useful if such mutations are recessive (which is nearly always the case).

With the realization of the inventive thought to apply the method disclosed herein for the various purposes disclosed above, the skilled person will be able to indeed apply these method for the above given purposes.

SUMMARY OF THE INVENTION

In one aspect there is provided for a method for removing genetic linkage between a first locus A and a second locus B present on a first plant chromosome in a plant or plant cell, wherein (meiotic) recombination between, and including, the location of said first locus A and the location of said second locus B on the chromosome is suppressed. The method comprises the steps of providing at least one plant cell comprising said first chromosome comprising said first locus A and said second locus B and further comprising at least a second chromosome, wherein said chromosomes are homologous or homeologous chromosomes of each other; introducing a double strand break in the first chromosome, wherein the double strand break in the first chromosome is introduced between said first locus A and said second locus B thereby providing a first part of the first chromosome comprising the first locus A and a second part of the first chromosome comprising the second locus B and introducing a double strand break in the second chromosome, thereby providing a first part of the second chromosome and a second part of the second chromosome. The double strand break in the first chromosome and/or the double strand break in the second chromosome is introduced by at least one site-specific nuclease, preferably selected from the group consisting of zinc finger nuclease, meganuclease, TAL-effector nuclease and the Cas9/crRNA/tracrRNA CRISPR system.

Optionally, but in certain embodiment preferred, the method further comprises identifying using the at least one plant cell obtained at least one plant cell wherein the genetic linkage between the first locus A and the second locus B on the first chromosome has been removed, and further, wherein the first part of the first chromosome comprising the first locus A is ligated to the second part of the second chromosome.

The double strand break in the first chromosome and/or the double strand break in the second chromosome is/are introduced by at least one site-specific nuclease, preferably selected from the group consisting of zinc finger nuclease, meganuclease, TAL-effector nuclease (TALENS) and the Cas9/crRNA/tracrRNA CRISPR system.

In a particularly preferred embodiment the method is performed wherein the first chromosome comprises said first locus A and said second locus B, wherein said first locus A is linked to a desirable trait of a first character and said second locus B is linked to a undesirable trait of said first character or a second character; and wherein said second chromosome does not comprise a locus that is identical to said second locus B linked to a undesirable trait of said first character or a second character, and; one double strand break is introduced between said first locus A and said second locus B on the first chromosome and at a corresponding locus or location in the second chromosome. This embodiment allows for the removal of linkage drag between desired and undesired traits commonly seen in (hybrid) plants.

Accordingly, there is also provided for a method for providing a plant P1 obtained from a plant P2, wherein said plant P2 is characterized by the presence of genetic linkage between a first locus A and a second locus B on a first chromosome, wherein (meiotic) recombination between, and including, the location of said first locus A and the location of said second locus B on the chromosome is suppressed, and wherein said plant P1 is characterized by the absence of said genetic linkage, the method comprising providing at least one plant cell comprising said first chromosome comprising said first locus A and said second locus B and further comprising at least a second chromosome, wherein said chromosomes are homologous or homeologous chromosomes of each other; introducing a double strand break in the first chromosome, wherein the double strand break in the first chromosome is introduced between said first locus A and said second locus B thereby providing a first part of the first chromosome comprising the first locus A and a second part of the first chromosome comprising the second locus B and introducing a double strand break in the second chromosome, thereby providing a first part of the second chromosome and a second part of the second chromosome, and; optionally, identifying from the at least one plant cell obtained at least one plant cell wherein the genetic linkage between the first locus A and the second locus B on the first chromosome has been removed, and further, wherein the first part of the first chromosome comprising the first locus A is ligated to the second part of the second chromosome. Plant P1 can thus be regenerated.

According to another aspect of the invention there is provided for the use of a site-specific nuclease, preferably selected from the group consisting of a zinc finger nuclease, a meganuclease, a TAL-effector nuclease and the Cas9/crRNA/tracrRNA CRISPR system for removing genetic linkage between a first locus A and a second locus B present on a first chromosome, wherein (meiotic) recombination between, and including, the location of said first locus A and the location of said second locus B on the chromosome is suppressed.

According to a final aspect of the invention there is provided for a plant, plant part, fruit or seed obtainable by or obtained by the method according to the invention, or the use according to the invention.

DESCRIPTION OF THE DRAWINGS

FIG. 2 provides the sequence of *Solanum pennellii* ALS2 locus (SEQ ID NO: 14). The ALS2 open reading frame is underlined. The target sequence for the ZFN is shown in bold italics.

FIG. 3 shows small deletions induced in protoplasts of the IL7-3 and M82 lines (SEQ ID NO: 15-22, respectively, in order of appearance). Upper line, sequence of the target site. The ZFN binding sites are underlined. The small deletions that were found in M82 and IL7-3 protoplasts are shown. The dashes represent missing nucleotides.

FIG. 4: M82 ALS2 and S. pennellii ALS2 sequences are shown (top) with the ZFN binding site underlined and the single nucleotide polymorphisms (SNP) between the loci shown in bold lowercase. The ZFN binding sites are underlined. The first SNP between the loci after the ZFN binding site is 449 bps downstream as is indicated. The primers used for all the PCR amplification were 11_13680 (S. pennellii ALS2 forward primer) and 12_07231 (M82 ALS2 reverse primer). M82 & IL7-3, sequence of cloned PCR products derived from transfection of protoplasts from the parental lines with pKG7402. F1, sequence of cloned PCR products derived from transfection of protoplasts from the F1 line with a pKG7381 (35S::GFP). F1×ZFN, sequence of cloned PCR products derived from transfection of protoplasts of the F1 line with pKG7402. The presence of small INDEL's at ZFN binding site is represented by missing nucleotides. Clones #1 and #2 were isolated using primers 12_11216+ 12_11217 in a non-selective PCR reaction. FIG. 4 discloses (SEQ ID NOS 23-35, respectively, in order of appearance).

DESCRIPTION

Definitions

Figure 1:
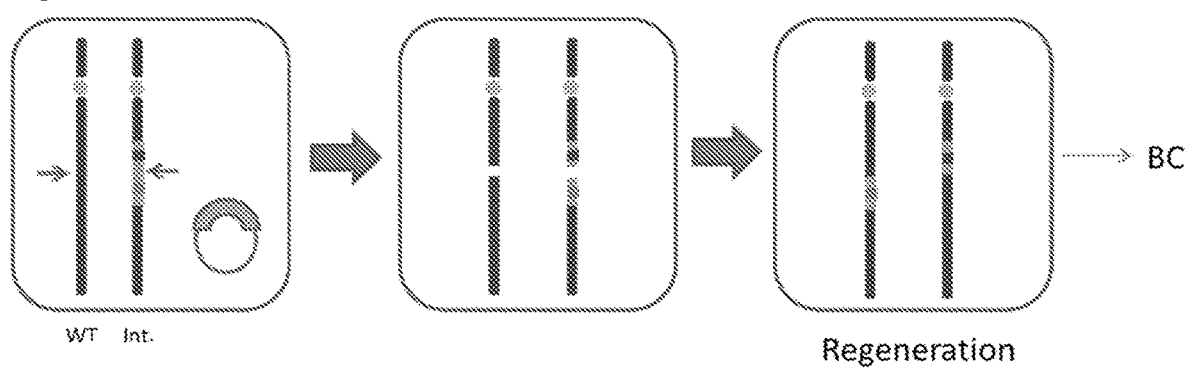
FIG. 1: Left panel: Two homologous chromosomes are indicated inside a single protoplast with the light grey section on one chromosome representing an introgression (light grey) from an unadapted wild species at which meiotic recombination does not occur (recombination suppression). The boxes in the introgression represent the locus giving the positive phenotype (black) and the locus giving the negative phenotype. The plasmid expressing the double-strand break-inducing enzyme is shown as a circle. The arrows represent the positions in the chromosome at which a DNA DSB is induced by the site-specific nuclease. Middle panel: DNA DSB is induced in both homologous chromosomes. Right panel: DSB repair leading to a reciprocal translocation. The positive and negative loci are no longer linked.

Unless defined otherwise, technical and scientific terms used herein have the same meaning as commonly understood by one of ordinary skill in the art to which this invention belongs. The practice of conventional techniques in molecular biology, biochemistry, computational biochemistry, cell culture, recombinant DNA, bioinformatics, genomics, sequencing and related fields are well-known to those of skill in the art and are discussed, for example, in the following literature references: Sambrook et al., Molecular Cloning. A Laboratory Manual, 2nd Edition, Cold Spring Harbor Laboratory Press, Cold Spring Harbor, N. Y., 1989; Ausubel et al., Current Protocols in Molecular Biology, John Wiley & Sons, New York, 1987 and periodic updates; and the series Methods in Enzymology, Academic Press, San Diego. For purposes of the present invention, the following terms are defined below.

As used herein, the singular forms "a," "an" and "the" include plural referents unless the context clearly dictates otherwise. For example, a reference to "a" DNA molecule may include a plurality of the same DNA molecules (e.g. 10's, 100's, 1000's, 10's of thousands, 100's of thousands, millions, or more molecules).

The term "and/or" indicates indicate that one or more of the stated cases may occur. In other words, a stated case may either occur alone or in combination with at least one of the stated cases, up to with all of the stated cases. The term and/or discloses each stated case alone, as well as the specific combination of a stated case with at least one of the other stated cases, up to with all of the stated cases.

In this disclosure, "comprises," "comprising," "containing" and "having" and the like can have the meaning ascribed to them in patent law and can mean "includes," "including," and the like; "consisting essentially of" or "consists essentially" likewise has the meaning ascribed in patent law and the term is open-ended, allowing for the presence of more than that which is recited so long as basic or novel characteristics of that which is recited is not changed by the presence of more than that which is recited, but excludes prior art embodiments.

As used herein, the term "allele(s)" means any of one or more alternative forms of a gene at a particular locus. In a diploid cell of an organism, alleles of a given gene are located at a specific location, or locus (loci plural) on a chromosome. One allele is present on each chromosome of the pair of homologous chromosomes. A diploid or plant species may comprise a large number of different alleles at a particular locus.

A "character" relates to a phenotypical quality of an organism. A character can manifest itself in different traits. For example, the plant can be a plant, having flower colour as a character, and the red or white flowers being the traits A and B of the character. Within the current invention, the character (or trait) can be any, as long as members of the organism having a first trait of the character can be phenotypically distinguished from members of the organism having a second trait of the character. This is not limited to only differences that can be directly observed by inspection of an organism, but also includes characters/traits that can become apparent upon further analysis of the organism, for example upon analysis of the resistance to certain circumstances, or upon analysis of the presence of particular metabolites in such organism.

"Genetic linkage" between loci on the same chromosome is understood by the skilled person to refer to those loci that are located relative to each other on the same chromosome such that they are normally inherited together during meiosis. For example, genes whose loci are nearer to each other are less likely to be separated onto different chromatids during chromosomal crossover, and are therefore said to be genetically linked. Another example is when loci are both located in the same segment of the chromosome characterized by "Suppression of (meiotic) recombination" (see below). Also in this case, the loci are likely to be inherited together during meiosis.

As used herein, the term "heterozygous" means a genetic condition existing when two different alleles reside at a specific locus. Conversely, as used herein, the term "homozygous" means a genetic condition existing when two identical alleles reside at a specific locus, but are positioned individually on corresponding pairs of homologous chromosomes in the cell.

The term "homeologous" or "homoeologous" chromosome, is used to describe the relationship of similar chromosomes brought together following inter-species hybridization and allopolyploidization, and whose relationship was completely homologous in an ancestral species. Two chromosomes are said to be homeologous when they are derived from two different genomes, but share characteristics such as similar nucleotide sequences, similar gene order synteny and are placed in corresponding positions in the karyograms of both genomes.

The term "homologous" chromosome is used to describe the relationship of similar chromosomes that pair at meiosis. Two chromosomes are homologous to each other when they are capable of forming chromosome pairs in meiosis through a synaptonemal complex.

The enzymatic reaction catalysed by a ligase enzyme in which two double-stranded DNA molecules are covalently joined together is referred to as ligation. The DNA molecule is said to be "ligated" by this reaction.

As used herein, the term "locus" (loci plural) means a specific place or places or a site on a chromosome where a gene or genetic marker is located.

The "genotype" is the genetic makeup of a cell, an organism, or an individual (i.e. the specific allele makeup of the individual) usually with reference to a specific character or trait under consideration.

A "phenotype" is the observable characteristics or traits of an organism such as its morphology, development, biochemical or physiological properties, phenology, behaviour, and products of behaviour. Phenotypes result from the expression of the genes of an as well as the influence of environmental factors and the interactions between the two.

The current disclosure is applicable to a wide range of plants, both monocots and dicots. Non-limiting examples include the Cucurbitaceae, Solanaceae and Gramineae, maize/corn (*Zea* species), wheat (*Triticum* species), barley (e.g. *Hordeum vulgare*), oat (e.g. *Avena sativa*), sorghum (*Sorghum bicolor*), rye (*Secale cereale*), soybean (*Glycine* spp, e.g. *G. max*), cotton (*Gossypium* species, e.g. *G. hirsutum, G. barbadense*), *Brassica* spp. (e.g. *B. napus, B. juncea, B. oleracea, B. rapa*, etc), sunflower (*Helianthus annus*), safflower, yam, cassava, alfalfa (*Medicago sativa*), rice (*Oryza* species, e.g. *O. sativa* indica cultivar-group or japonica cultivar-group), forage grasses, pearl millet (*Pennisetum* spp. e.g. *P. glaucum*), tree species (*Pinus*, poplar, fir, plantain, etc), tea, coffea, oil palm, coconut, vegetable species, such as pea, zucchini, beans (e.g. *Phaseolus* species), cucumber, artichoke, asparagus, broccoli, garlic, leek, lettuce, onion, radish, lettuce, turnip, Brussels sprouts, carrot, cauliflower, chicory, celery, spinach, endive, fennel, beet, fleshy fruit bearing plants (grapes, peaches, plums, strawberry, mango, apple, plum, cherry, apricot, banana, blackberry, blueberry, citrus, kiwi, figs, lemon, lime, nectarines, raspberry, watermelon, orange, grapefruit, etc.), ornamental species (e.g. Rose, Petunia, Chrysanthemum, Lily, Gerbera species), herbs (mint, parsley, basil, thyme, etc.), woody trees (e.g. species of *Populus, Salix, Quercus, Eucalyptus*), fibre species e.g. flax (*Linum usitatissimum*) and hemp (*Cannabis sativa*), or model organisms, such as *Arabidopsis thaliana*.

For the purposes of the present invention, the term "recombination" is used to indicate the process by which genetic material between two loci is exchanged.

"Suppression of (meiotic) recombination": the meiotic recombination between two loci on the same chromosome in a hybrid individual is suppressed when less than one crossover or recombination event occurs in 2000 offspring individuals after selfing or backcrossing of the hybrid plant.

In biology, "a trait" relates to any phenotypical distinctive character of an individual member of an organism in comparison to (any) other individual member of the same organism. Within the context of the current invention the trait can be inherited, i.e. be passed along to next generations of the organism by means of the genetic information in the organism. "Trait of the same character" or "trait of said character": anyone of a group of at least two traits that exist (or became apparent) for a character. For example, in case of the character "colour of the flower", phenotypical manifestations might comprise blue, red, white, and so on. In the above example blue, red and white are all different traits of the same character.

Throughout this application, various references are cited in parentheses to describe more fully the state of the art to which this invention pertains. Full bibliographic information for each citation is found at the end of the specification, immediately preceding the claims. The disclosure of these references is hereby incorporated by reference into the present disclosure in their entirety.

DETAILED DESCRIPTION

The current invention provides a new and inventive method for removing genetic linkage between loci present on a chromosome, making it possible to no longer rely on classical breeding methodology or classical marker-assisted breeding. In particular the methodology disclosed herein allows for achieving recombination in somatic cells at parts of the chromosome characterized by having suppressed (meiotic) recombination, i.e. parts that, under meiotic conditions are normally inherited together. The method allows, in one aspect, for reciprocal chromosome translocation (cross-over; exchange) between homologous and/or homeologous chromosomes in somatic cells in areas or parts of the chromosome that are characterized by having suppressed (meiotic) recombination. This, for example, allows for the first time, to efficiently remove genetic linkage between two loci on the same chromosome and both located in such "supressed (meiotic) recombination" part of the chromosome. In addition, the method allows for this in somatic cells, is DNA sequence independent and does not depend on meiosis or mitosis.

More in particular there is provided for a method for removing genetic linkage between a first locus A and a second locus B present on a first plant chromosome in a plant or plant cell, and wherein (meiotic) recombination between, and including, the location of said first locus A and the location of said second locus B on the chromosome is suppressed, the method comprising the steps of:

(a) providing at least one plant cell comprising said first chromosome comprising said first locus A and said second locus B and further comprising at least a second chromosome, wherein said chromosomes are homologous or homeologous chromosomes of each other;

(b) introducing a double strand break in the first chromosome, wherein the double strand break in the first chromosome is introduced between said first locus A and said second locus B thereby providing a first part of the first chromosome comprising the first locus A and a second part of the first chromosome comprising the second locus B
and
introducing a double strand break in the second chromosome, thereby providing a first part of the second chromosome and a second part of the second chromosome, and;

(c) optionally, identifying using the at least one plant cell obtained under step (b) at least one plant cell wherein the genetic linkage between the first locus A and the second locus B on the first chromosome has been removed, and further, wherein the first part of the first chromosome comprising the first locus A is ligated to the second part of the second chromosome, and wherein the double strand break in the first chromosome and/or the double strand break in the second chromosome is introduced by at least one site-specific nuclease, preferably selected from the group consisting of zinc finger nuclease, meganuclease, TAL-effector nuclease and the Cas9/crRNA/tracrRNA CRISPR system.

With the method genetic linkage between to loci A and B, present on the same chromosome is removed. In other words, after the method according to the invention the two original loci A and B are less likely to be inherited together during subsequent meiosis and are in fact not present together on the same chromosome. In a preferred embodiment, locus A and locus B are present on the same chromosome arm.

Locus A and locus B on the first chromosome may be a gene, a promoter, a genetic marker or any sequence present on the first chromosome. The locus may or may not be mapped as being the locus for a particular biological trait. In some embodiments, locus A and/or locus B are a gene and/or part of a gene.

The method is preferably performed on a chromosome present in a plant cell, preferably a plant protoplast and preferably in the presence of the other naturally occurring components of such plant cell, including the complete set of chromosomes of such plant cell.

In a preferred embodiment, the plant cell is a protoplast. Methods for obtaining and maintaining plant protoplasts are readily available to the skilled person. It was found that the most efficient method of inducing (sequence specific) DNA DSB's in plant cells is through the use of plant protoplasts. Protoplasts are individual plant cells that lack the primary and secondary cell walls and are generated by incubating plant parts with a fungus-derived enzyme mixture. Any DNA, such as plasmids, can then be introduced into protoplasts by chemical treatments and any gene of interest present on the plasmid whose expression is driven by a suitable plant promoter can be expressed at high levels due to the thousands of plasmid copies that enter each cell. Gene expression is preferably transient, lasting e.g. 24-36 hours, as the plasmid is unable to replicate and becomes degraded over time. Additionally, integration of the plasmid in the plant genome is rare. /pct Individual plant protoplasts can be induced to divide to form undifferentiated cell clumps called calli and these in turn can be induced to regenerate leaves and shoots which can then be rooted to produce plants. A protoplast based system is ideal for the production of DNA DSB's using any of the methods described herein. The site-specific nuclease can be placed on the plasmid, expressed to a high level, and high amount of site-specific protein produced that is able to induce the required DNA DSB. Protoplasts can be isolated in large numbers (millions per day) and transfected with plasmid DNA en masse, and the calli derived from these transfected protoplasts are derived from a single protoplast cell and so do not suffer from chimaerism.

The locus A and the locus B are however characterized in that they are localized on said first chromosome in a part, area or segment that is characterized in that (meiotic) recombination of that part, area or segment is suppressed. As described herein, "suppressed meiotic recombination" is meant to indicate that meiotic recombination between the two loci on the same chromosome in a hybrid individual is less than one crossover or recombination event occurring in 2000 offspring individuals after selfing or backcrossing of the hybrid plant. In a preferred embodiment this is less than one crossover or recombinant event occurring in 2500, 5000 or 8000 offspring individuals. A person skilled in the art is aware on how to determine this.

In the method, a double strand break is introduced in the first chromosome, comprising said first locus A and said second locus B. The position or locus where such double strand break is introduced is between said first locus A and B. By introducing a double strand break between locus A and B, the chromosome is divided in at least two parts, preferably no more than two parts; one part comprising said locus A and one part comprising said locus B. In the context of the current invention, when reference is made to a first part or second part of said chromosome this may indicate either the part that now comprises the centromere (i.e. that was in the original chromosome towards (and including) the centromere), or the part that, by the introduction of the double strand break, now is separated from the centromere (i.e. the part that was further away from the centre of the chromosome, i.e. closer to the end of the chromosome (arm), relative to the other part that is formed due to the introduction of a double strand break). If, in the context of the current invention a first part of the first chromosome is ligated to a second part of the second chromosome, this indicates that a part of the first chromosome that is closer to the centromere of the first chromosome is ligated to a part of the second chromosome that is further away from the centromere of the second chromosome, relative to the other part that is formed due to the introduction of the double strand break in said chromosome(s) or the other way around. In other words, in a re-ligated chromosome comprising a first part of a first chromosome and a second part of a second chromosome, in one embodiment the first part was closer to the centromere of the first chromosome and the second part was further away from the centromere of the second chromosome, relative to the other part of the same chromosome formed by the introduction of the double strand break.

It was surprisingly found that, when performing the above steps, plant cells may be identified, using molecular techniques, or simply by regenerating a plant from such cells, wherein the genetic linkage between said first locus A and said second locus B has been removed, and wherein there has occurred a cross-over (exchange) between the at least two homologous or homeologous chromosomes such that locus A is present of a first chromosome and locus B is present on said second homologous or homeologous chromosome. Put otherwise, wherein the homologous or homeologous chromosomes have been re-organized in that an exchange or cross-over occurred between the at least two chromosomes, and wherein the locus A and locus B, although being located in an area of the chromosome with supressed (meiotic) recombination have been separated.

Optionally, therefore, at least one cell may be identified, after performing the above steps (a) and (b) wherein the genetic linkage between the first locus A and the second locus B on the first chromosome has been removed, and further, wherein the first part of the first chromosome comprising the first locus A is ligated to the second part of the second chromosome. Alternatively, in some embodiments, the obtained cells after step (b) may be regenerated into plants, and optionally subsequently selfed, and the plants thus obtained may be used to phenotypically screen for the removal of the genetic linkage between locus A and B, for example in case locus A and locus B are linked to particular trait(s) that can be observed.

Preferably step (c) of the method above is performed, i.e. is part of the method according to the invention. The skilled person is, based on the disclosure herein, well aware of how to identify such at least one cell. For example, individual protoplasts may first be separately propagated, after which a few of the propagated (clonal) protoplasts may be analysed, for example using standard DNA sequencing, or amplification or hybridisation techniques for the re-ligation of the two part of the two chromosomes, and/or phenotyping the offspring, and/or fluorescent in-situ hybridisation (FISH)..

In a preferred embodiment, when performing step (c) above, the method further comprises identification of those cells wherein in addition also the second part of the first chromosome is ligated to the first part of the second chromosome. Again, as above, the skilled person is well aware on how to perform such identification.

In a particularly preferred embodiment of the methods disclosed herein the plant cell selected is such that the second chromosome does not comprise a locus that is identical to said first locus A and/or does not comprise a locus that is identical to said second locus B. In other words, although the second chromosome may have an allele of the same locus A and/or B, it must have at least some sequence difference with the locus/allele present in the first chromosome. For example, the first chromosome comprises a locus A or B that may be a first allele of a certain gene, and the second chromosome may comprise another allele for the same gene. Preferably, in such embodiment, the allele on the first chromosome and the second chromosome are related to a different phenotype.

In another embodiment of the methods disclosed herein, the distance between said first locus A and said second locus B present on said first plant chromosome is between one base pair and the length of the entire chromosome. As has been disclosed above, the locus A and locus B on the first chromosome are both in (a same) area/part/segment of the chromosome that is characterized by suppressed (meiotic) recombination. A particular additional advantage of the current invention is that now such loci can be easily separated, while still providing surviving and normal plants even if such loci are either very close to each other or far removed.

In the methods disclosed herein, the double strand break in the first chromosome and/or the double strand break in the second chromosome is/are introduced by at least one site-specific nuclease preferably selected from zinc finger nuclease, meganuclease, TAL-effector nuclease (TALENS) and the Cas9/crRNA/tracrRNA CRISPR system.

Whereas genotoxic agents that introduce DNA breaks and modifications randomly throughtout the genome, the (endo) nucleases used in the current invention can nowadays be rationally designed to recognize and bind to a specific DNA sequence at which a DNA DSB is subsequently induced.

For the current invention four technologies/nuclease systems to introduce the DSB are preferred: (1) meganucleases, (2) zinc finger nucleases (ZFN), and (3) TAL effector nucleases (TALENs) and (4) the Cas9/crRNA/tracrRNA CRISPR system.

Meganucleases, including such homing endonulceases as I-SceI, can be mutated to confer an altered DNA sequence affinity (Belfort and Roberts, 1997, Nucleic Axids Res. 25: 3379-3388; Chevalier and Stoddard, 2001, Nucleic Acids Res. 29: 3757-3774) and their activity has been reported in plants (Kirik, 2000, EMBO J. 19, 5562-566). Meganucleases are also sometimes referred to as LAGLIDADG Homing Endonucleases ("LAGLIDADG" disclosed as SEQ ID NO: 13) (LHE's; Stoddard et al (2011) Structure 19:7-15). Meganucleases differ from Zinc Finger Nucleases and TALENs (see below) in that they are naturally occurring gene-targeting proteins that form homodimers comprising two identical subunits each about 160 to 200 amino acid residues in size. It has been suggested they may also function as a single peptide of two tandem repeat monomers joined together by a linker sequence (Stoddard, 2011). Meganucleases generally recognize a target site of about 20 to 30 base pairs. For an overview of meganucleases and methods to assess mutated meganucleases for activity and altered target specificities reference is made to Stoddards et al (2011). In addition, the use of meganucleases has, for example, been described in WO2011154159 and EP2522723. The meganuclease or the pair of meganucleases, as well as all the other nucleases used in the current invention may be introduced in the plant cell and subsequently (transiently) expressed therein, and using methods well aware to the skilled person. For example from a chimeric gene or a pair of chimeric genes, each comprising a plant expressible promoter linked to a coding region encoding the meganuclease or one of the pair of meganucleases, and further operationally linked to a DNA region involved in transcription termination and polyadenylation functional in a plant cell.

For the purposes of the present invention, the term "zinc finger nuclease" or "ZFN" refers to a chimeric protein molecule comprising at least one zinc finger DNA binding domain effectively linked to at least one nuclease capable of cleaving DNA. Cleavage by a ZFN at a target locus results in a double stranded break (DSB) at that locus. Zinc finger nucleases consist of two domains, an array of zinc finger domains and a nuclease domain, usually derived from the IIS-type restriction enzyme FokI. These type IIS restriction enzymes, such as FokI, recognize specific DNA sequences and cleave several base pairs downstream of the recognition site. Each zinc finger domain can be engineered to recognize a specific 3 bps triplet and by linking together a number of these a longer DNA sequence can be specifically recognized. The FokI domain must dimerise before cutting DNA and so two ZFN proteins are designed to target sequences on the opposite DNA strands separated by a short spacer region of 5-6 bps. Binding of both of the ZFN proteins to their respective target sequence brings both FokI domains opposite each other on the DNA helix in the spacer region where a DNA DSBs is then produced. Many studies have shown that ZFN are effective in inducing small INDEL's at an endogenous target sequence in many different plant species (Curtin (2012) The Plant Genome, 5, 42-50). Custom-made zinc finger nucleases are commercially available under the name CompoZr from Sigma-Aldrich. The use of zinc finger nucleases in plants has, for example, been described in WO03087341 and WO2011052539. The ZFN used for the current invention, as well as all the other nucleases used in the current invention, may be introduced in the plant cell and subsequently (transiently) expressed therein, and using methods well aware to the skilled person. For example from a chimeric gene or a pair of chimeric genes, each comprising a plant expressible promoter linked to a coding region encoding the zinc finger nuclease or one of a pair of zinc finger nucleases, and further operationally linked to a DNA region involved in transcription termination and polyadenylation functional in a plant cell. The publication US2012/0196370 teaches that ZFNs can be used to create defined deletions in a eukaryotic genome. In this approach ZFNs whose target sites are separated by up to 120 Kbps and introduced into cells together with a linear "donor" molecule which has at either end a region of sequence homology each of the separated ZFN target sites. After treatment of animal cell lines with these reagents products could then be amplified whereby the region between the ZFN target sites had been replaced by the donor molecule, producing an effective deletion of the intervening sequence. In this case the mitotic HR pathway is used due to the regions of sequence homology present at the ends of the donor molecule. The publication suggests that the donor molecule is essential to first, drive the accuracy of the mitotic HR reaction and second, to increase the frequency of the mitotic HR reaction. This is thought to be necessary because the frequency of translocations obtained when just using the ZFNs is too low for practical application. In contrast to what is taught in the literature, the current inventors found that specific translocations between plant chromosomes can be produced when only a single ZFN pair is used to generate the DSBs. In contrast to the publication US2012/0196370 our experiments utilize the NHEJ pathway to generate translocations as we observe at the chromosome fusion points small deletions that are characteristic for this recombination pathway. When a DNA DSB is induced in only one of the plant chromosomes the DNA ends are rejoined by the NHEJ pathway resulting in small deletions. The frequency of these small deletions (present in 10% of the cells) is made up of two components, the cutting efficiency of the ZFN pair and efficiency at which the DSB is repaired by the NHEJ pathway. In this case a single DSB is induced on one chromosome so that the DNA ends are in close proximity, resulting in the 10% efficiency. However, for a translocation to occur DSBs must be produced on two chromosomes that are spatially separated in the nucleus and the interaction of these DNA ends is unlikely resulting in a very low frequency of translocation formation. However, we have found that efficiency of translocation formation (0.8%) in plant cells by the NHEJ pathway is unexpectedly high, only 12 fold lower than the repair of adjacent DNA ends, and therefore allows easy isolation of individual cells that had undergone this recombination process. In addition, our method in plant cells does not require a "donor" molecule as the frequency and accuracy of translocation formation using the NHEJ pathway is already high enough according to our invention for practical application. Thus, the method according to the invention does not need to use such linear donor molecule or donor polynucleotide as described in US2012/0196370.

TALENs are site specific nucleases derived from TAL effectors produced by Xanthomonas species which cause a variety of different plant diseases. During the infection of a plant by Xanthomonas species the TAL effector proteins are introduced into the plant cell. TAL effectors consist of a number of repeating protein domains, each of which is able to specifically recognize and bind to one of the 4 DNA nucleotides (A,T,G,C). Different combinations of these domains are present in different TAL effectors and each one binds to a unique DNA sequence in the plant genome, often in plant gene promoters. pathogen Once bound to the plant DNA the TAL effector influences plant gene expression to enhance the bacterial pathogenicity. The domains specific for each nucleotide have been identified and arrays of these domains can be produced which have high binding affinity for any DNA sequence (Christian, 2010, Genetics 186: 757-761; Cermak et al., 2011, Nucleic Acids Res 39:e82; Bogdanove and Voytas, 2011, Science 333: 1843-1846; Boch, 2011, Nature Biotechnology 29:135-136). Commercial custom-made TALENs are available from Cellectis Bioresearch. These arrays are then fused to the nuclease domain of FokI to create a TALEN and, similar to ZFN, two TALEN proteins are used to induce a DNA DSB in a spacer region at the target sequence. Several papers have described the use of TALEN's to create mutations at the target sequence species (Curtin (2012) The Plant Genome, 5, 42-50). The TALENS used for the current invention, as well as all the other nucleases used in the current invention, may be introduced in the plant cell and subsequently (transiently) expressed therein, and using methods well aware to the skilled person. For example from a chimeric gene or a pair of chimeric genes, each comprising a plant expressible promoter operably linked to a coding region encoding the TALENS nuclease or one of a pair of TALENS nucleases, and further operationally linked to a DNA region involved in transcription termination and polyadenylation functional in a plant cell. The use of TAL-effector (TALENS) has, for example, been described in WO201107224.

The CRISPR technology (also herein referred to as the Cas9/crRNA/tracrRNA CRISPR system.) is derived from bacteria where it is used as a system to defend against invading molecular pathogens such as plasmids and bacteriophages. Specific loci in the bacterial genome consist of arrays of short sequences derived from the genomes of molecular pathogens which are the result of previous infections. Small RNA's (crRNAs) are produced from these loci that interact with the tracrRNA and these RNA molecules together then target the Cas9 protein to the specific complementary sequence in the molecular pathogen's genome. The Cas9 protein has nuclease activity and is able to produce a specific DNA double strand break (DSB) at the target sequence in the pathogen genome which then becomes degraded. Expression of both the Cas9 protein (nuclease), tracrRNA and crRNA (the components of the CRISPR system) targeting a genomic sequence in the cells of plants and animals creates targeted DSBs at the genomic target sequence that is often mis-repaired by the cellular DNA machinery, resulting in a small insertion or deletion (INDEL) (Feng et al. (2013) Cell Res. 1: 4; Li et al. (2013) Nat. Biotech. 31: 689-691; Nekrasov et al. (2013) Nat. Biotech. 31: 691-693; Shan et al. (2013) Nat. Biotech. 31: 686-688). An INDEL in the coding sequence of a gene or even in an intron often leads to loss of gene function. For practical purposes, the tracrRNA and crRNA are usually combined into one chimeric guide RNA (sgRNA); this combination of RNAs is included in the definition of the Cas9/crRNA/tracrRNA CRISPR system.

Site specific nucleases can induce targeted DSBs at a high efficiency and thus plants containing INDELs in the target sequence can be easily identified. Genome engineering through the use of site specific nucleases such as the CRISPR systems has many applications, especially in polyploidy species, and is becoming increasingly important for crop improvement.

Although in principle one or more of the above-discussed nucleases may be used, alone or in combination, it is preferred that the double strand break in the first chromosome and/or the double strand break in the second chromosome is introduced by the same site-specific nuclease, the same zinc finger nuclease, the same meganuclease, the same TAL-effector nuclease, or the same the Cas9/crRNA/tracrRNA nuclease system. In other words, it is preferred to target at a sequence in both the first and the second chromosome that may targeted by the same nuclease, for example because the target sequence is identical. Recognizing such a target in both the first chromosome and the second chromosome is within the skills of the skilled person, and will not be difficult since the first and second chromosome are homologous or homeologous chromosomes sharing parts of the chromosome having high levels of identity, e.g. 100%.

It will be clear to the skilled person, and based on the disclosure herein, in a preferred embodiment of the methods disclosed herein no more than one double strand break is introduced in the first chromosome and no more than one double strand break is introduced in the second chromosome.

In another preferred embodiment of the methods according to the invention
i. the first chromosome comprises said first locus A and said second locus B, wherein said first locus A is linked to a desirable trait of a first character and said second locus B is linked to a undesirable trait of said first character or a second character; and
ii. wherein said second chromosome does not comprise a locus that is identical to said second locus B linked to a undesirable trait of said first character or a second character, and;
iii. one double strand break is introduced between said first locus A and said second locus B on the first chromosome and at a corresponding locus or location in the second chromosome.

This embodiment of the method according to the invention provides for overcoming linkage drag. The method provides for separating of a locus A that is linked to a favourable treat from a locus B that is linked to an unfavourable trait. Both locus A and B may be a genetic marker linked to said desired (A) or undesired (B) trait or may be (in) the gene that is causally linked to the desired or undesired trait. The traits associated or linked with the locus A and B may or may not be of the same character.

As disclosed above, in a particularly preferred embodiment of the methods disclosed herein the plant cell selected is a such that the second chromosome does not comprise a locus that is identical to said first locus A and/or does not comprise a locus that is identical to said second locus B. In other words, although the second chromosome may have an allele of the same locus A and/or B, it must have at least some sequence difference with the locus/allele present in the first chromosome. For example, the first chromosome comprises a locus A or B that may be a first allele of a certain gene, and the second chromosome may comprise another allele for the same gene. In the context of the current embodiment the skilled person understands that the second chromosome preferably does not provide a locus that is identical to said undesired locus B at the first chromosome, or comprises a locus B that is an undesired allelic variant of such undesired locus B. In other words, by this method according to the invention the first chromosome is modified as such that the undesired locus B originally present on the chromosome is removed and replaces by a corresponding part of the chromosome obtained from the second chromosome, and not containing said locus B linked to an undesired trait.

Non-limiting examples of undesirable traits may be a trait selected from the group consisting of: a trait that negatively influences the desirable trait of the first character, reduced yield, reduced resistance to disease or pests, reduced growth, reduced size, reduced amount of seeds, reduced resistance against stress, including salt, heat, cold, water and drought stress. However, as will be understood any trait of a character may be considered undesirable, depending on the purpose of the breeders or skilled person, alone or relative to the desired trait associated to the locus A.

In a further embodiment of the method according to the invention, the method further comprises regenerating a plant from a plant cell obtained after step (b) or step (c) and generating seed from said regenerated plant by selfing or crossing with another plant and growing a plant from the obtained seed and optionally, screening said plant obtained for removal of genetic linkage. As explained above, the skilled person is well aware how to perform these steps and how to screen for the removal of genetic linkage.

Preferably the provided plant cell is a somatic plant cell, preferably a protoplast, and/or a plant cell obtained from a hybrid. The plant cell may be obtained from any suitable plant, for example as specifically disclosed herein. The plant cell may be derived from, for example diploid, triploid, tetraploid, pentaploid, hexaploid, octaploid, decaploid, dodecaploid or an amphidiploid plant.

In line of the disclosure herein, and taking into account all preferences and modifications discussed herein and in possession of the skilled person, there is also provided for a method for providing a plant P1 obtained from a plant P2, wherein said plant P2 is characterized by the presence of genetic linkage between a first locus A and a second locus B on a first chromosome,
wherein (meiotic) recombination between, and including, the location of said first locus A and the location of said second locus B on the chromosome is suppressed, and wherein said plant P1 is characterized by the absence of said genetic linkage, the method comprising
(a) providing at least one plant cell comprising said first chromosome comprising said first locus A and said second locus B and further comprising at least a second chromosome, wherein said chromosomes are homologous or homeologous chromosomes of each other;
(b) introducing a double strand break in the first chromosome, wherein the double strand break in the first chromosome is introduced between said first locus A and said second locus B thereby providing a first part of the first chromosome comprising the first locus A and a second part of the first chromosome comprising the second locus B
and
introducing a double strand break in the second chromosome, thereby providing a first part of the second chromosome and a second part of the second chromosome, and;

(c) optionally, identifying using the at least one plant cell obtained under step b) at least one plant cell wherein the genetic linkage between the first locus A and the second locus B on the first chromosome has been removed, and further, wherein the first part of the first chromosome comprising the first locus A is ligated to the second part of the second chromosome, and wherein the double strand break in the first chromosome and/or the double strand break in the second chromosome is introduced by at least one site-specific nuclease, preferably selected from the group consisting of zinc finger nuclease, meganuclease, TAL-effector nuclease and the Cas9/crRNA/tracrRNA CRISPR system.

Again, preferably step (c) is performed.

According to another aspect there is provided for the use of a site-specific nuclease, preferably selected from the group consisting of a zinc finger nuclease, a meganuclease, a TAL-effector nuclease and the Cas9/crRNA/tracrRNA CRISPR system, for removing genetic linkage between a first locus A and a second locus B present on a first chromosome, wherein (meiotic) recombination between, and including, the location of said first locus A and the location of said second locus B on the chromosome is suppressed. Preferably there is provided for the use wherein said first locus A is linked to a desirable trait of a first character and said second locus B is linked to an undesirable trait of said first character or a second character.

Also provided is for the use of a site-specific nuclease, preferably selected from a zinc finger nuclease, a meganuclease, a TAL-effector nuclease and the Cas9/crRNA/tracrRNA CRISPR system for removing linkage drag.

In a last aspect there is provided for a plant, plant part, fruit or seed obtainable by or obtained by a methods or uses according to the invention. In a preferred embodiment there is provided for a group of at least 2 of such plant, plant part, fruit or seed.

In summary, the disclosed invention, in a non-limiting embodiment, involves inducing crossovers between homologous or homeologous parental chromosomes in somatic plant protoplasts through the use of site-specific nucleases that may induce a specific DNA DSB at the same sequence on both chromosomes. This may be achieved by isolating plant protoplasts and then introducing the site-specific nuclease present on a plasmid into the protoplasts by a chemical treatment. The site-specific nuclease protein is then produced in the protoplast and induces the DNA DSB's. It is believed that the NHEJ system may repair these DSB's by ligating the free DNA ends from the different chromosomes together, resulting in an exchange of chromosome arms, also known as a reciprocal translocation. Site-specific nucleases can be designed to induce DSB's at any desired sequence, and thus a reciprocal translocation can be induced at any point along the homologous parental chromosomes. One large advantage over meiotic recombination is that the joining of DNA ends using the method according to the invention is sequence independent and therefore using this approach there is no limitation on the regions that can be targeted or exchanged. Therefore, this approach is ideal for breaking linkage drag in; for example, introgressions which, due to sequence differences, do not recombine during meiosis (are suppressed). There are many examples of important traits in commercially important crops species, such as viral TMV and TYLCV resistance in tomato, which are located on large introgression fragments with severe linkage drag which has a negative effect on the plant yield. As these resistances are valuable, the yield losses are accepted but it will be very beneficial to both plant breeders are growers to break such linkage drag to further increase plant yield.

The ability to create plants containing introgressions with a defined size is also of great use to plant breeders in general. Populations of plants, each containing a defined introgression from a wild unadapted plant species can be produced and used for crop improvement and gene discovery. Genes responsible for novel traits can be mapped more efficiently by splitting up the introgression on which they lie into smaller parts and repeating this until the position of the gene of interest has been defined. As the generation of targeted translocations is sequence independent, plant introgression libraries can be generated more quickly and precisely all the genomic regions can be equally represented. This decreases the need for screening large F2 populations for the desired crossovers, meaning that fewer facilities such as greenhouse space are required. This method can also be applied to the breeding of allo-polyploid species such as tobacco, rapeseed or wheat. Allo-polyploid plant species are often the result of an ancient hybridization event between two or more diploid plant species whereby the separate different genomes do not recombine during meiosis. For instance, *Brassica napus* consists of an A and C genome which do not mix during meiosis. Therefore, a particular chromosomal region on either of the genomes cannot be made completely homozygous through selfing. Protoplasts of *B. napus* can be isolated and transfected with a plasmid construct carrying a site-specific nuclease that induces a DSB at the same position on both the A and C chromosomes. The cell may then generate a reciprocal translocation between the A and C genomes which would not be possible to achieve through meiotic recombination. The subsequent regenerated plants can then be selfed any plants that are fully homozygous for the translocation in both genomes identified. Targeted translocations can also be very useful for the manipulation of DNA sequences at the gene level. If a specific promoter has been identified that is more active in a wild unadapted plant species than in the cultivated species then targeted translocations can be used to transfer the active promoter into the genome of the cultivated species. This can be achieved by crossing the two species to produce a F1 line, isolating protoplasts from this, and then expressing a site-specific nuclease in these protoplasts that induces a DSB in both homologous chromosomes at a position just before the transcription start of the gene of interest. The resulting targeted translocation will join the upstream sequences, including the active promoter, to the gene of interest this altering its pattern and level of transcription. Similarly, site-specific nucleases can be designed to introduce DSB's at introns of genes present on different homologous chromosomes. A targeted translocation between these DSB's will result in the exchange of gene domains between the homologous chromosomes and the formation of chimeric genes containing domains from each chromosome. In this case, the small deletions produced by the NHEJ system are located in the intron itself and so are unlikely to inhibit gene function.

EXAMPLES

Example 1

Inducing a Targeted Translocation at Chromosome VII in Tomato Protoplasts

The experimental setup for generating targeted translocations in tomato cells is shown in FIG. 1. The approach uses a site specific nuclease, in this example a zinc finger nuclease, which induces a DNA double strand break (DSB) at the same or corresponding genomic position on both of the homologous chromosomes. A translocation between the chromosomes can then be formed when these two DSB's are repaired by joining the DNA ends together from the other chromosome, thus exchanging the chromosome arms. To detect the formation of translocations, PCR primers were designed that specifically amplify the ZFN cut site on each chromosome. Once a translocation has been formed these junctions can be specifically amplified by using different combinations of these forward and reverse primers. For specific primer design, sequence differences must be present flanking the ZFN cut site on each chromosome. This was achieved by using a tomato line carrying an introgression on chromosome VII from the wild tomato species *Solanum pennellii*. This introgression region contains the ZFN target site in the *S. pennellii* ALS2 gene (SpALS2) and also enough sequence differences with the wild type ALS2 (WT ALS2) to make specific primer design possible. The experiment was performed by creating a F1 hybrid heterozygous for the ALS locus by crossing the WT tomato (M82) with the *S. pennellii* chromosome VII introgression line IL7-3. Protoplasts were then produced from this F1 hybrid and transfected with a plasmid construct which expresses the ZFN that induces the DSB at both the WT ALS2 and SpALS2 loci. Using our PCR approach we were able to detect cells in which a reciprocal translocation had occurred. Surprisingly, such events were detectable at a relatively high frequency (0.8%) which was unexpected because the DNA DSBs were located on different chromosomes. This is the first reported evidence that site specific nucleases are able to induce reciprocal translocations in plant cells and a demonstration that such events occur at a relatively high frequency. We then went on to grow individual plant protoplasts to callus and genotyped these calli using PCR to identify those with the desired translocation. Such calli can be regenerated into plants and would show a loss of linkage between the markers flanking the introgression fragment. This approach can be used to decrease the size of an introgression fragment in somatic plant protoplasts in a homology independent manner.

Zinc Finger Nuclease Construct

For our experiments the plasmid pKG7402 was used. This plasmid contains 2 zinc finger nuclease genes designed to bind and induce a DNA double strand break at the tomato acetolactate synthase (ALS) genes (ALS1 and ALS2). ALS1 is located on the short arm of chromosome III and ALS2 is located on the long arm of chromosome VII.

Plant Material

*Solanum lycopersicum* line (IL7-3) containing an introgression from the tomato wild species *Solanum pennellii* on chromosome VII was used. This introgression fragment is approximately 56 cM in size and makes up the majority of the long arm of this chromosome (Eshed, Y & Zamir, D. (1995) Genetics 141: 1147-1162) and includes the ALS2 gene of *S. pennellii*. Plants homozygous for this introgression fragment were backcrossed to the parent line (M82) and F1 seeds were collected. These were then sterilized and germinated on synthetic medium (MS20: MS medium+ vitamins (Duchefa) 4.4 g/l, sucrose 20 g/l, micro agar 8 g/l) in high jars at 16/8 h photoperiod of 2000 lux at 25° C. and 60-70% RH. The parent M82 and the homozygous IL7-3 lines were also treated in the same way and maintained as sterile plants in tissue culture. After 3-4 weeks the mature leaves were harvested for the production of protoplasts.

Protoplast Isolation and Transfection

Isolation and regeneration of tomato leaf protoplasts has been previously described (Shahin (1985) Theor. Appl. Genet. 69: 235-240; Tan (1987) Theor. Appl. Genet. 75: 105-108; Tan (1987) Plant Cell Rep. 6: 172-175) and the solutions required can be found in these publications. Briefly, 1 g of freshly harvested leaves were placed in a dish with 5 ml CPW9M and, using a scalpel blade, cut perpendicular to the main stem every mm. These were transferred a fresh plate of 25 ml enzyme solution (CPW9M containing 2% cellulose onozuka RS, 0.4% macerozyme onozuka R10, 2.4-D (2 mg/ml), NAA (2 mg/ml), BAP (2 mg/ml) pH5.8) and digestion proceeded overnight at 25° C. in the dark. The protoplasts were then freed by placing them on an orbital shaker (40-50 rpm) for 1 hour. Protoplasts were separated from cellular debris by passing them through a 50 μm sieve, and washing the sieve 2× with CPW9M. Protoplasts were centrifuged at 85 g, the supernatant discarded, and then taken up in half the volume of CPW9M. Protoplasts were finally taken up in 3 ml CPW9M and 3 ml CPW18S was then added carefully to avoid mixing the two solutions. The protoplasts were spun at 85 g for 10 minutes and the viable protoplasts floating at the interphase layer were collected using a long Pasteur pipette. The protoplast volume was increased to 10 ml by adding CPW9M and the number of recovered protoplasts was determined in a haemocytometer. For transfection with a plasmid construct, the protoplast suspension is centrifuged at 85×g for 10 minutes at 5° C. The supernatant is discarded and the protoplast pellet resuspended to a final concentration of 106.mL-1 in KCl wash medium. In a 10 mL tube, 250 μL of protoplast suspension+/−40 μg of pure plasmid DNA and 250 μl of PEG solution (40% PEG4000 (Fluka #81240), 0.1M Ca(NO3)2, 0.4M mannitol) are gently but thoroughly mixed. After 20 min. incubation at room temperature, 5 mL cold 0.275 M Ca(NO3)2 is added drop wise. The protoplast suspension is centrifuged for 10 min at 85×g at 4° C. and the supernatant discarded. After PEG treatment tomato protoplasts were embedded in alginate solution for regeneration. 2 ml of alginate solution was added (mannitol 90 g/l, CaCl2.2H2O 140 mg/l, alginate-Na 20 g/l (Sigma A0602)) and was mixed thoroughly by inversion. 1 ml of this was layered evenly on a Ca-agar plate (72.5 g/l mannitol, 7.35 g/l CaCl2.2H2O, 8 g/l agar) and allowed to polymerize. The alginate discs were then transferred to 4 cm Petri dishes containing 4 ml of K8p culture medium and incubated in the dark at 30° C. for 7 days. The alginate discs were then cut into 5 mm thick strips and layered on solid regeneration medium TM-DB (TM2 basal 2.5 g/l (Duchefa), Nitsch vitamins 110 mg/l, sucrose 50 g/l, micro agar 8 g/l, 2,4-D 0.2 mg/l, BAP 0.5 mg/l, pH5.8) for 3 weeks. Regenerated calli were then picked with tweezers and placed individually on GM-ZG medium (MS macro+micro powder (Duchefa) 4.3 g/l, Nitsch vitamins 110 mg/l, mannitol 36.4 g/l, sucrose 2.5 g/l, micro agar 8 g/l, zeatin 1 mg/l, GA3 1 mg/l, pH5.8). These were then sampled for DNA isolation when they had reached approximately 7 mm. Upon shoot regeneration the calli were transferred to MS-ZI medium (MS+vitamins (Duchefa) 4.4 g/l, sucrose 20 g/l, micro agar 8 g/l, zeatin 2 mg/l, IAA 0.1 mg/l, pH5.8). After 2-3 weeks shoots were excised and transferred to rooting medium (MS+vitamins (Duchefa) 4.4 g/l, sucrose 20 g/l, micro agar 8 g/l, 0.5 mg/ml IBA, pH5.8) and subsequently to the greenhouse.

Sequencing of the *S. pennellii* ALS2 Locus

Chromosomal DNA was isolated from the homozygous IL7-3 line (DNeasy kit, Qiagen) and the Genome Walker kit (Clontech) was used to determine the sequence of the *S. pennellii* ALS2 locus as per the manufacturer's instructions.

Briefly, 500 ng of genomic DNA was digested overnight with a restriction enzyme (DraI, EcoRV, PvuII or StuI), and the Genome Walker adaptors were ligated. The ALS2 specific nested primers 11_11533 (5'-TGG-GAATGGTGGTTCAGTGGGAGGA-3' (SEQ ID NO: 1)) and 11_11534 (5'-GGTGGTTCAGTGGGAGGATCGAT-TCT-3' (SEQ ID NO: 2)), designed on a conserved sequence in the S. lycopersicum ALS2 ORF, were used to amplify the 3' end of the S. pennellii ALS2 locus. Correspondingly, the nested primer pair 11_11536 (5'-CGTAGCTCCCGGACCAGATGTAGCA-3' (SEQ ID NO: 3)) and 11_11537 (5'-ATGTAGCAATACAAACACCAGG-GAACCCA-3' (SEQ ID NO: 4)) were used to amplify the 5' end of the ALS locus. The PCR products were excised from the gel and sequenced. Based on these sequences, additional primers (11_13680 (TCACCCCTTCACCTTACC (SEQ ID NO: 5)) and 11_13681 (CCTTCACATTTAACCAAAGC (SEQ ID NO: 6))) were designed that amplified the intervening region and used to complete the sequencing of the locus (FIG. 2). In this way it was demonstrated that the ZFN target site in ALS2 was conserved in both the M82 and the IL7-3 lines.

Design of ALS2 locus specific primers

Figure 2A:
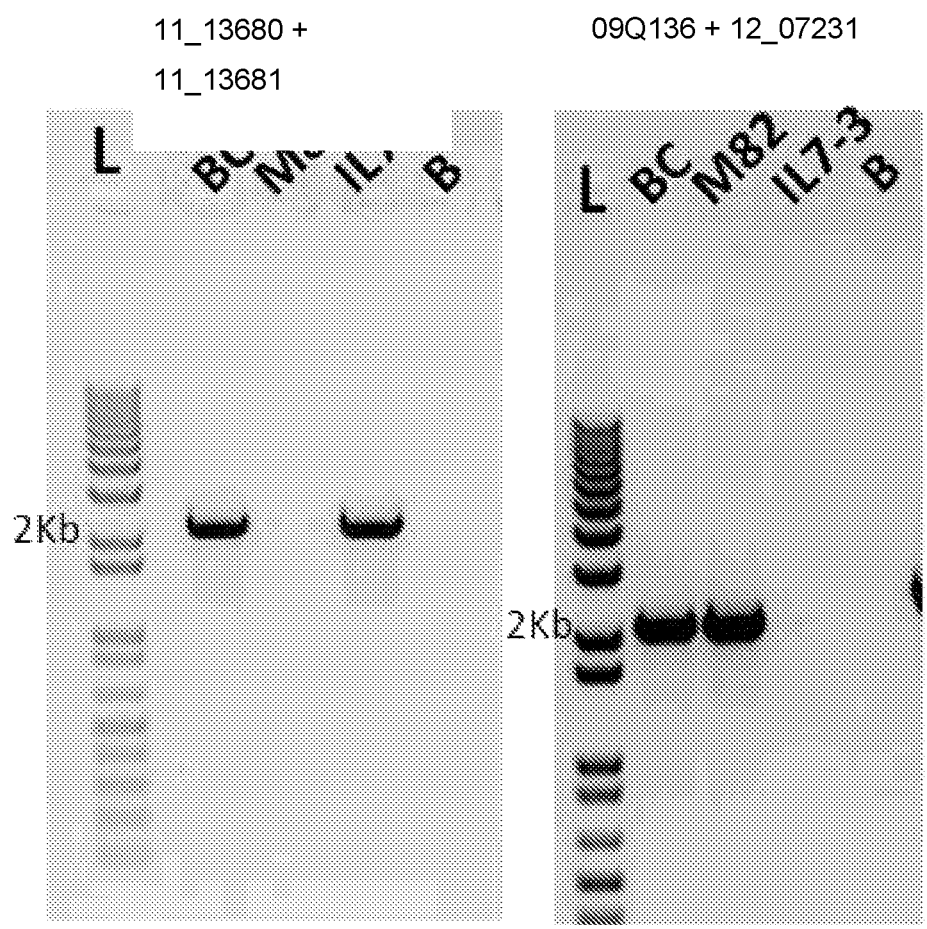
FIG. 2a shows the results of testing of primers specifically amplifying either the *Solanum pennellii* ALS2 locus (left panel) or the WT ALS2 locus (right panel). L, ladder; BC, F1 line derived from a IL7-3×M82 cross; M82, WT tomato line; IL7-3, line containing *S. pennellii* introgression on chromosome VII; B, water control.

Alignment of the S. pennellii and M82 ALS2 sequence enabled us to identify sequence differences which could be exploited for the design of specific primers which would selectively amplify only one of the alleles and which would amplify a PCR product that includes the ZFN target site. To amplify the S. pennellii ALS2 locus we used the primers 11_13680+11_13681 and for the M82 ALS2 locus the primers 09Q136 (GAAAGGGAAGGGGTTAAGG (SEQ ID NO: 7)) and 12_07231 (CTTCAGTAGAGCCCTTGC (SEQ ID NO: 8)) were used. The results are shown in FIG. 2a and show that these primers amplified a band of the correct size in the parental lines IL7-3 and M82 and that both loci were present in the F1 line derived from a cross of these two parents (line BC).

Induction of INDELs at the S. pennellii ALS2 locus

Protoplasts were isolated from both the IL7-3 line and M82 plants and transfected either with plasmid pKG7402 or with a plasmid carrying a 35S::GFP cassette (pKG7381). After 12 hours the protoplasts transfected pKG7381 were observed under the fluorescent microscope to assess GFP expression. This was equivalent in both the IL7-3 and the M82 protoplasts (data not shown), demonstrating that the S. pennellii introgression in line IL7-3 did not affect transformation. After 48 hours the protoplasts were harvested by centrifugation and genomic DNA was isolated using the DNeasy kit (Qiagen). A PCR reaction was then performed on this DNA using primers 09Q132 (CTTGTG-GAGGCACTTGAA (SEQ ID NO: 9)) and 09Q133 (CCGGACCAGATGTAGCAATA (SEQ ID NO: 10)) which amplify a 205 bps fragment of the ALS2 locus that includes the ZFN target site. The PCR product was then purified and cloned into a vector (pCR2.1:Blunt, Invitrogen) and transformed to One Shot Chemically Competent E. coli cells (Invitrogen) as per the manufacturer's instructions and plated on LB medium supplemented with 50 µg/m1 kanamycin (Duchefa). A PCR was subsequently performed on individual 96 bacterial colonies using the same primers and the resulting PCR products were analysed by High Resolution Melting curve analysis on a Roche Light Cycler apparatus to identify PCR products with aberrant melting characteristics. Such clones were then taken for sequencing and the results are shown in FIG. 3. For both the IL7-3 and M82 lines, approximately 10% of the PCR products derived from the population of transfected protoplasts contained an INDEL at the ZFN target site. The size of these INDELs in both lines was also comparable and thus we can conclude that the S. pennellii ALS2 locus can be targeted as efficiently as the M82 ALS2 locus. As a control we also analysed 96 PCR products derived from the pKG7381 transfection. None of these showed aberrant melting characteristics and when two were sequenced they did not show any alterations to the sequence (data not shown).

Targeted Translocations at the ALS2 Locus in Tomato Protoplasts

Protoplasts were isolated from in vitro grown F1 plants (derived from a M82×IL7-3 cross). In addition, we also isolated protoplasts from in vitro grown M82 and IL7-3 plants. The protoplasts were transfected with 40 µg of plasmid pKG7402 (or 40 µg of pKG7381 as a control) and maintained in liquid medium for 48 hours. The protoplasts from each transfection were then harvested by centrifugation (800 rpm, 10 minutes) and genomic DNA was then isolated from these protoplast populations using the DNeasy kit (Qiagen). To detect the presence of translocations in the protoplast population, combinations of the locus specific primers were used. For instance, the combination of the S. pennellii ALS2 primer (11_13680) and the M82 primer (12_07231) should only amplify chromosomes which have undergone a translocation and will produce a PCR product that includes the translocation junction at the position of the ZFN target site. A PCR reaction using these primers was performed on all the protoplast DNA samples using the following cycling conditions {95° C. 2'; [95° C. 30", 60° C. 30", 72° C. 2']×40; 72° C. 5'} in a reaction consisting of 1 µl genomic protoplast DNA, 5 µl 5× Herculase Fusion buffer (Agilent), 0.3 µl 100 mM dNTPs, 1.25 µl primer 11_13680, 1.25 µl primer 12_07231, 0.25 µl Herculase 11 Fusion enzyme (Agilent) & 15.95 µl water. Electrophoresis of the PCR products on a 1% agarose gel showed that all samples produced a band of the expected size but that the intensity of the band was stronger in the F1 plant samples treated with pK7402 (data not shown). As we observed a PCR product in the control samples, this suggested that the primer combination 11_13680+12_07231 was able to generate an aspecific PCR product from the unaltered S. pennellii and M82 ALS2 loci, but that the PCR product from the treated F1 protoplasts may be stronger as in addition it contains PCR products generated from translocation junctions. The 2.2 kbps PCR products from both the treatments and the controls were excised from the gel and purified using the Qiagen Gel isolation kit. The PCR products were then cloned using the Zero Blunt PCR ligation kit (Invitrogen) following the manufacturer's instructions and the resulting plasmids containing the cloned products were purified from E. coli TOP10 cells and the complete 2.2 kbps PCR products were sequenced. The results are shown in FIG. 4. The primers were indeed able to amplify an ALS2 PCR product from the control samples but sequencing showed that these always were derived from either the WT ALS2 locus (M82) or from the SpALS2 locus (IL7-3). Analysis of two PCR products derived from the F1 protoplasts transfected with the control plasmid (pKG7381) showed that both loci had been amplified in this PCR reaction. All PCR products from the controls showed the expected sequence. The PCR products derived from the F1 hybrid protoplasts treated with pKG7402 all showed a small INDEL at the ZFN binding site, similar to those that we had earlier observed when protoplasts from the parental lines were treated with pKG7402. However, for each of these 2.2 kbps PCR products the SNP's upstream of the ZFN binding site indicated that this was S. pennellii ALS2 sequence while the SNP's downstream of the ZFN binding site were derived from the M82 ALS2 sequence, as we would expect for a translocation junction fragment. Therefore, this provided good evidence that in the population of protoplasts cells were present that had undergone a targeted translocation at the ALS2 locus between the *S. pennellii* introgression and the WT M82 chromosome VII resulting in an exchange of chromosome arms and breaking of linkage in the introgression fragment.

To quantify how many protoplasts in the treated population contained a targeted translocation, we attempted to quantify the number of PCR products which have this characteristic *S. pennellii*/M82 ALS2 chimeric organization. We performed a PCR on the genomic DNA using the primers 12_11216 (CTTCCACCCTTCTTCCCAAATC (SEQ ID NO: 11) and 12_11217 (TGCCAACTCCTGCA-CATTCA (SEQ ID NO: 12)). These primers are not specific and so amplify a 1.3 kbps product from both the WT ALS2 and the *Sp*ALS2 loci. Such a PCR reaction thus consists of *Sp*ALS2, WT ALS2, and targeted translocation products. To determine the relative amounts of each these products in the PCR reaction, and thus the efficiency of the targeted translocation process itself, the products from the PCR reaction were cloned and genotyped. The 1.3 kbps PCR product includes the ZFN binding site and two diagnostic restriction sites located either side. Upstream of the ZFN binding site, an A→G change in the *S. pennellii* ALS2 sequence creates a *Hind*III restriction site. Downstream of the ZFN binding site a C→A change in the *S. pennellii* ALS2 sequence creates a *Mse*I site. These sites were used as a basis for a CAPS assay to genotype PCR products for the ALS2 sequence flanking the ZFN binding site. The 1.3 kbps PCR product was cloned using the Zero Blunt PCR Ligation kit as per the manufacturer's instructions. Individual bacterial colonies were then resuspended in 50μl water, heated at 95° C. for 5 minutes and then 1 μl of this was used in a nested PCR with the primers 09Q132+09Q133 or with 09R037+09R040 which were subsequently digested with *Hind*III or *Mse*I respectively. The presence or absence of both the *Hind*III and the *Mse*I sites was indicative of an unaltered ALS2 locus (either *Sp*ALS2 or WT ALS2) whereas a cloned PCR product having only one of these PCR products may have been derived from a targeted translocation event. In total 249 bacterial colonies were genotyped for the presence of only one of these restriction sites and five were eventually identified. For confirmation, the 1.3 kbps PCR products of these five clones were sequenced. Of the five PCR products, we found two that had the expected organization (FIG. 4). The first, clone #1, showed the *S. pennellii* ALS2 sequence upstream of the ZFN binding site and the M82 ALS2 sequence downstream. For clone #2 this was reversed. Therefore, we can conclude that the efficiency of targeted translocation formation in our experimental setup is approximately 2 in 249 (0.8%). This suggests that only a limited number of protoplasts need to be screened to isolate cells with targeted translocations.

Isolation of Tomato Plants with Targeted Translocations

Protoplasts were isolated from leaves of the F1 hybrid line and transfected with 40 μg of plasmid pKG7402. For further development they were then embedded in alginate discs which were then incubated in 4 ml K8p medium for 7 days. The discs were then sliced into 5 mm strips which were then placed on solid TM-DB medium (2-4D, BAP) for further development of the microcalli. After 3 weeks growth 800 calli were picked with forceps and transferred to fresh TM-DB medium. We have shown that the translocation junctions always contain a small INDEL at the ZFN cut site and so we first screened all of the calli for this. For genotyping, a small piece of tissue was scraped from each developing callus using a plastic pipette tip and then resuspended in 20 μl of dilution buffer from the Phire Plant Direct PCR Kit (Thermo Scientific). For direct PCR on this material 1 μl of the dilution was taken and mixed with 10 μl 2× reaction buffer, 2 μl of the primers 12_11216 and 12_11217 (5 pmol) 0.2 μl of the Phire polymerase and water to a final reaction volume of 20 μl. The PCR conditions used were; 98° C. 5 mins, {98° C. 5 secs, 62° C. 5 secs, 72° C. 1.5 minutes}×40, 72° C. 5 mins. These PCR products were then diluted 200× in water and 1 μl of this was used in a nested PCR to amplify the ZFN cut site (1 μl PCR product, 5 μl 10× reaction buffer, 0.5 μl dNTPs (20 mM), 1 μl 09Q132 (5 pmol), 1 μl 09Q133 (5 pmol), 0.2 μl AmpliTaq (5 U/μl) and 41.3 μl water with the cycling conditions 94° C. 2 mins, {94° C. 30 secs, 55° C. 30 secs, 72° C. 30 secs}×30, 72° C. 5 mins. This generates a 200 bps PCR fragments including the ZFN cut site that can be screened for the presence of INDELs. These PCR reactions were also carried out on material from the F1 line to generate control PCR products. To detect calli with INDELs at the ZFN cut site, 4 μl of each 200 bps PCR product was mixed with 4 μl of the control PCR product and 1 μl of both TE and LC Green. The melting characteristics of this mixture were then determined using the Gene Scanning protocol of the Roche Light Cycler. We identified 53 samples with aberrant melting characteristics indicative of an INDEL at the ZFN cut site. The 1.3 kbps products from these 53 calli were then cloned using the Zero Blunt PCR cloning kit (Invitrogen). Subsequently 4 bacterial colonies from each ligation were genotyped for the presence of the HindIII and MseI sites as described above. From a single callus, TT1 and TT2, we were able to show that all of the bacterial clones tested lacked one of the restriction sites, demonstrating that this cell had undergone a reciprocal targeted translocation. These clones were sequenced and we were able to show that, similar to the sequences derived from the protoplasts, a targeted translocation had occurred in these calli. The frequency at which these calli were identified (0.25%) is in the same range as previously determined and remains unexpectedly high.

Marker Analysis of RFPL's Flanking the *S. pennellii* Introgression

The calli TT1 and TT2 can then be transferred to shooting medium and the subsequent shoots induced to form roots. The plants are then transferred to the greenhouse for further genotyping. Seed is collected from the plant TT1 and germinated in soil. Leaf material is harvested from seedlings and DNA isolated. To demonstrate that the markers TG20 and TG143 are no longer linked in the progeny the seedlings are analyzed for the presence of these markers. Selfing of the F1 plants, where the two markers are present on the same chromosome flanking the introgression, would be expected to give progeny where 25% lack either of the markers and 75% are positive for both markers. In a plant containing a targeted translocation the linkage between the markers has already been broken in the protoplasts. When the progeny of such plants are analysed we would expect 50% to have both markers (in this case located on different chromosomes), 25% to contain only marker TG20 and 25% contain only marker TG143. Marker segregation analysis can be performed on the progeny of the TT1 and TT2 plants. Therefore, the transient expression of a site specific nuclease such as a ZFN in tomato protoplasts can induce reciprocal targeted translocations that give viable plants and can be transmitted to the next generation. This approach can be used to break any form of linkage between two DNA sequences in a sequence independent manner.

Example 2

Breaking the Linkage Drag at the TYLCV Locus

Tomato yellow curl leaf virus (TYLCV) is a devastating tomato disease caused by a begamovirus and transmitted by whitefly. TYLCV infection is common in warm (sub)tropical regions and this limits tomato growth in these regions. Resistance to TYLCV infection has been found in several wild tomato species (Ji et al. (2007) in Tomato Yellow Leaf Curl Virus Disease (Czosnek, H., ed). Netherlands: Springer, pp. 343-362). Currently, five resistance loci are used in breeding, Ty1 to Ty5. The Ty1 locus from *S. chilense* LA1969 was the first resistance locus to be mapped and is linked to the Ty3 locus on chromosome 6 and has been incorporated into several commercially available varieties. However, the Ty1 resistance locus suffers from linkage drag as it is accompanied by undesirable traits such as autonecrosis. The Ty1 locus is located in the pericentromeric region of chromosome 6 and is located on a 17 MB introgression fragment which suffers from severe suppression of recombination. Verlaan et al. (2011, Plant J 68: 1096-1103) studied recombination at the Ty1 locus in 3000 F2 plants but were unable to detect any recombination events in their population over the majority of the introgression fragment. This appeared to be due to several chromosomal rearrangements in *S. chilense* LA1969 which inhibit recombination in this region during meiosis. As the production of targeted translocations is homology independent, this can be used to decrease the size of the Ty1 locus in order to break the linkage drag and simplify the fine mapping of the Ty1 locus.

Several BAC's from *S. lycopersicum* have been identified that are present in the Ty1 introgression fragment (Verlaan et al., 2011, Plant J 68: 1096-1103). We used the sequence of one of these (H208D24) to identify genes that are likely to represent single copy sequences in the tomato genome. This BAC carries the tomato homolog of the *A. thaliana* gene PRH75 (Plant RNA Helicase 75, At5g62190) annotated as Unigene SGN U268902. While this BAC was chosen arbitrarily, any other sequence in the introgression region that is present on both chromosomes could also be used to perform these experiments. To identify nucleotide differences at this locus between *S. lycopersicum* and *S. chilense* LA1969 Genome Walking can be performed on this locus in both plant species. This allows the design PCR primers specific for the two SGN U268902 loci. Subsequently a TALEN construct can be designed that binds and cuts between the primer sites to validate its activity.

A plant line heterozygous for the Ty1 introgression is then cultivated in vitro and protoplasts are isolated and transfected with the TALEN plasmid DNA. Tomato protoplasts are then regenerated to callus and screened using combinations of the SGN U268902 locus specific primers to identify calli containing translocation junctions. These are then regenerated to plants and selfed and the segregation of markers flanking the SGN U268902 locus are determined. It is then possible to demonstrate that the size of the Ty1 introgression fragment had been reduced and these plants can be analysed further for loss of linkage drag and for an assessment of the recombination frequencies at the shortened introgression fragments.

Example 3

Creating an Introgression of a Defined Size in Tomato Breeding Material and Fine Mapping of a Gene Responsible for Early Fruit Ripening A tomato line, ER43, carrying a locus on chromosome I responsible for early fruit ripening can be identified. Through marker analysis it can be established that the locus is located between the AFLP markers MM101 and MM107, which are separated by 527 kbps. The complete sequence of this region is available and so a series of target sequences can be selected spaced by 100 kbps which, based on BLAST analysis, are single copy sequences in the tomato genome. Primers are designed flanking these target sequences and used to amplify the corresponding loci in the tomato line Moneymaker to firstly confirm that the target sequences are identical in both lines and secondly to identify sequence differences around these target sequences in the two tomato lines which can be exploited for the design of specific primers. Subsequently, five TALEN constructs are designed to produce DSBs at these target sequences. The TALEN sequences are then synthesized and cloned into a plasmid construct fusing the TALEN with a promoter sequence that is active in tomato protoplasts, such as the tomato AA6 promoter. Protoplasts of the ER43 and Moneymaker lines are transfected with each TALEN plasmid, incubated for 24 hours in a suitable liquid medium, and then harvested by centrifugation. The genomic DNA is then isolated from each population of transfected protoplasts and each of the five target sequences is then amplified using chromosome specific primers. The PCR products are then analysed for the presence of INDELs at the target sequence, which would be present in around 10% of each batch of treated protoplasts. This will demonstrate that the TALEN constructs are active in the cell and are able to induce DSBs at the target sequences of both tomato lines. Lines ER43 and Moneymaker are then crossed to produce an F1 line which is maintained under sterile conditions in tissue culture and used for the production of protoplasts. These protoplasts are then transfected with the TALEN constructs and 1000 calli derived from each transfection are grown and then genotyped for the presence of a translocation at the target sequence using different combinations of the chromosome specific PCR primers. The calli containing these targeted translocations are then regenerated into plants and then selfed to create F2 plants that are homozygous for each translocation. These are then phenotyped to identify the chromosome fragment carrying the early ripening locus. A physical map is then constructed of this region and the gene responsible for the early ripening phenotype can be identified.

Example 4

Targeted Translocations in *Brassica napus*

Oliseed rape, or canola (*Brassica napus*) is an amphidiploid species formed from the interspecific hybridization of *Brassica rapa* (the A genome) and *Brassica oleraceae* (the C genome). Selective pedigree breeding has been intensively used to improve both yield and seed quality in this crop. Pedigree breeding involves the selection and inbreeding of superior F2 and later-generation individuals resulting from crosses between pairs of established cultivars. However, due to the limited number of F2 plants screened the end products of the breeding process often contain large amounts of the parental genomes that give a negative effect on agronomic traits. This has been demonstrated in the *B. napus* type "Tapidor" that even after multiple generations of backcrossing still contained 29% of one of the parental genomes (Sharpe & Lydiate, 2001, Genome 46: 461-468). It is possible to calculate the probability that a hypothetical F2 individual, derived from a F1 carrying distinct donor and elite alleles in all genomic units, does not contain any fixed donor genotype. This has been estimated to occur approximately once in 81825 F2 plants (Sedcole, T. R. (1977) Crop Sci. 17: 667-668). In contrast, pedigree breeding programs in oilseed rape generally only select from between 1000 and 2000 F2 plants, resulting in the selection of an individual containing a large amount of unlinked donor genotype. Combined with the practice of producing doubled haploids to increase the breeding speed, parental genotypes can become very quickly homozygous and fixed, even when not linked to the locus of interest.

Figure 5:
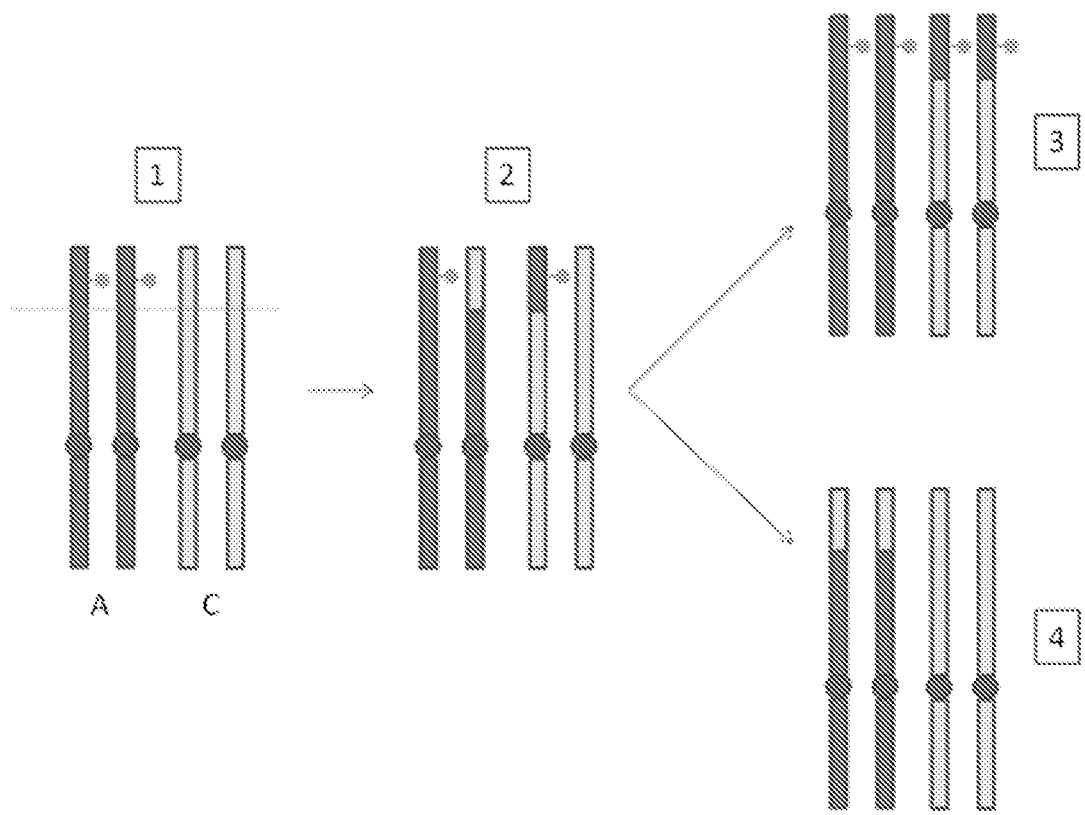
FIG. 5 schematically shows targeted translocations in *Brassica napus*. 1, the A (dark grey) and C (light grey) genomes are indicated. The locus to be made homozygous is indicated by a circle. A site-specific nuclease is expressed in the cell and induced a DSB in all 4 chromosomes at the position of the dotted line. 2, a targeted translocation occurs between the A and C genomes. 3, after selfing the translocation region and the locus of interest is homozygous. 4, part of the chromosome arm from the C genome becomes homozygous.

Due to the amphidiploid nature of *B. napus*, meiotic recombination between the A and C genomes is prevented during meiosis. This is also the case for other amphidiploids species such as tobacco (*Nicotiana tabacum*), durum wheat (*Triticum durum*), common wheat (*Triticum aestivum*) and cotton (*Gossypium hirsutum*). Considering an example in *B. napus*, agronomically important traits from parental lines can be introduced into commercial lines through a breeding program which results in the parental locus, usually in a homozygous state, being present on one of the genomes (e.g. on the A genome). However, due to the restrictions on recombination between the genomes during meiosis, the corresponding locus on the C genome is unchanged. If this region also happens to carry some negative phenotypes, or decreases the effectiveness of the phenotype conferred by the parental locus on the A genome, then this cannot be easily resolved through conventional breeding. By inducing a targeted translocation between the A and C genomes using site directed nucleases it is possible to produce a plant which is homozygous for the parental locus on both the A and C genomes (Schematically shown in FIG. 5). Another possible application of this technology in polyploids is the transfer of mutagen induced mutations between genomes to create fully homozygous lines. Mutation breeding is a common method of plant improvement. It involves the treatment of plants, usually seed, with a mutagen such as ethyl-methanosulfate (EMS) that generates C to T changes throughout the genome. Mutated populations of plants are then grown, selfed, and in the following generation (M2) the plants are screened for altered phenotypes (forward screen) or selected on the basis of induced mutations in the gene of interest when the sequence is known (reverse screen). In many cases a mutation is required that confers a (complete) loss-of-function phenotype and this requires the identification of two plant lines, each carrying a null mutation in the gene of interest in one of the genomes. These plants can then be crossed, the F1 selfed, and F2 plants identified which are homozygous for both null mutations on both genomes. This is a very time consuming and expensive approach and becomes harder with species such as hexaploid wheat when dealing with three genomes. To avoid having to isolate independent mutations in each genome and then performing crosses we disclose that targeted translocations can be induced to transfer an induced (null) mutation between genomes and quickly reach a homozygous state (FIG. 5).

The experiments are focused on inducing a targeted translocation between the *B. napus* chromosome 8 A and C genomes. The *B. napus* line "Tapidor" is selected for these experiments as it carries a large introgression fragment on chromosome 8 of the A genome from the *B. napus* line "Bronowski" which contains many sequence differences with the corresponding region on chromosome 8 of the C genome. A unique gene present in both the A and C genomes is then identified and sequenced in the "Tapidor" line to identify sequence differences. Based on these, primers are designed which only amplify the A or C genome locus. To induce a DNA DSB at both the loci on the A and C genomes, a TALEN construct is designed. The A and C loci are screened for a sequence identical to both and TALENs are designed to bind and cut at this sequence. The TALEN's are cloned into a plasmid vector with a constitutive plant promoter (35S) and are introduced into *B. napus* "Tapidor" protoplasts using PEG transfection. After 48 hours, DNA is isolated from the protoplasts and the locus specific primers are used to generate PCR products which are sequenced to demonstrate that the TALEN construct is able to induce INDEL's at the target site. The experiment is then repeated and individual *B. napus* calli are regenerated and genotyped for the presence of targeted translocations by using combinations of the A and C genome locus specific primers. Individual calli can be identified that have targeted translocations at the expected positions and also different sized INDELs in chromosome 8 (e.g. 4 bps in the A genome, 3 bps in the C genome) representing different INDELs at the translocation junctions in the hybrid A and C chromosomes. Plants are then regenerated from these calli and grown to maturity. The next generation is then screened for seedlings that are homozygous for these INDELs and these are also homozygous for the remainder of the chromosome arm.

Example 5

Fusion of Locus Domains Using Targeted Translocations

The plant line IR3 has a strong resistance to a wide range of insects due to the presence of an insecticidal compound at high concentration in its trichomes. This high concentration is achieved by a high expression of one of genes (IK4) involved in the biochemical synthesis of this compound. The high expression is achieved by a novel promoter which drives high transcriptional activation in a trichome specific manner. The plant line IR12 also contains the IK4 gene, but is susceptible to insect feeding. Molecular analysis has shown that the IK4 gene is not expressed in the trichomes of IR12 and that this is due to nucleotide differences in the promoter of the IK4 gene in the IR12 line which leads to its inactivation. The goal of these experiments was to restore the high trichome specific expression of the IK4 gene in the IR12 line by inducing a targeted translocation between the lines, resulting in the fusion of the IR3 promoter with the IK4 gene from line IR12. A target sequence is identified located 20 bps upstream of the IK4 ORF and a TALEN is designed to create a DSB at this site. The TALEN is then cloned behind a suitable promoter for plant expression and the resulting plasmid is then transfected to protoplasts from both the IR3 and IR12 lines. As described in example 3, in this way we are able to confirm that the TALEN expression is able to induce a DSB at the target sequence in both plant lines. A F1 line is then made by crossing the IR3 and IR12 lines and is then used to produce protoplasts that are then transfected with the TALEN construct. As described in other examples, specific primers amplifying either the IR3 or the IR12 locus are used in different combinations to identify calli in which a targeted translocation has occurred. These calli are then regenerated into plants and then backcrossed to the IR12 parent plant several times, selecting for the targeted translocation in each generation, to reach a situation where the plant is isogenic to the IR12 parent except for the desired translocation. Using quantitative RT-PCR it can be shown that that in this line the precise fusion of the IR3 promoter to the IR4 IK4 gene has restored high IK4 expression in the trichomes and subsequent phenotyping demonstrates that this plant shows strong resistance to a wide range of insects.

This example demonstrates that translocations can be used to fuse promoter or other regulatory sequences to genes of another line and thus achieve novel expression patterns giving valuable phenotypes.

Example 6

Creating Novel Open Reading Frames Using Targeted Translocations

Resistance to fungal pathogens is often conferred by the class of leucine rich repeat (LRR) genes located in resistance gene clusters distributed throughout the plant genome. Plant line M17 contains a LRR resistance gene (LRR12) conferring specific resistance to the race 1 of the fungal pathogen that causes the disease late blight. The plant line P15 carries a similar resistance gene cluster located at the same position on the chromosome. In P15, the resistance gene most similar in sequence to LRR12, named LRR63, is located at the same position in the cluster but has a different amino acid sequence. As a consequence the LRR63 gene confers resistance to fungal race 2 but not the race 1. Neither of these resistance genes confers resistance to the fungal race 3. Our hypothesis is that novel resistance to fungal race 3 can be achieved by combining domains of the LRR12 and LRR63 genes. The sequence of both of these genes is known and the introns are analysed for sequences that were present in both LRR12 and LRR63. A site specific nuclease is then designed that is able to induce a DSB at this target sequence. The site specific nuclease is then cloned behind a promoter providing expression in plant protoplasts and the resulting plasmid is then used to transfect protoplasts from both the plant lines M17 and P15. As described in more detail in the other examples included herein, we are able to demonstrate that the site specific nuclease is able to produce DSBs at the intron target sequences in both LRR12 and LRR63. A F1 line is then produced by crossing the M17 and P15 lines and is maintained in sterile conditions in tissue culture. Protoplasts are then isolated from the F1 line and transfected with the plasmid encoding the site specific nuclease. Individual protoplasts are then regenerated to calli and these are genotyped with combinations of specific primers designed for LRR12 or LRR63 to detect calli in which a targeted translocation has occurred. As the translocation has been targeted in an intron, the small INDELs that are produced during the translocation only remove part of the intron sequence and therefore do not affect the gene open reading frame. The translocation results in the fusion of domains of the LRR12 gene with domains of the LRR63 gene, creating a novel gene conferring new resistances. The calli with the translocation are regenerated into plants and it can be demonstrated that the new chimeric open reading frame is made up of domains from both LRR12 and LRR63 and that it provides novel resistance to fungal race 3. This example demonstrates how targeted translocations can be used to join domains from different genes together to create novel genes conferring important new phenotypes.

Example 7

Simultaneous Induction of Targeted Translocations and Inhibition of Meiosis

Targeted translocations can be induced between homoeologous chromosomes in a F1 hybrid using site specific nucleases. The individual calli can then be regenerated to produce plants that then proceed through normal meiosis leading to a normal F2 population with genomic segments from both parental plants. Extensive backcrossing is then required to obtain isogenic lines for phenotyping which can take years and involves multiple rounds of population screening. An isogenic line can be obtained in a single generation when meiotic crossovers are inhibited in the original plant allowing the parental chromosomes to segregate randomly in the gametes. Most gametes will be nonviable due to abnormal chromosome number, but a small percentage will contain all the chromosomes of the desired parent and when used in a direct backcross with the required parent will generate an isogenic line in a single generation. The targeted translocation to be produced can be any of those described in examples 1 to 6. Protoplasts can be produced from F1 plants and simultaneously transfected with two plasmids. The first plasmid carries a site specific nuclease, driven by a promoter active in plant protoplasts, that produces the desired targeted translocation as already described. The second plasmid carries a different site specific nuclease, driven by a second promoter active in plant protoplasts that is designed to create a DSB in a gene, Dmc1, involved in crossover formation during meiosis. Repair of this DSB will produce small INDELs in the meiotic gene leading to a complete loss of gene function. Calli are then selected containing the desired targeted translocation and these are then screened for additional homozygous INDEL mutations at the target sequence of Dmc1. These calli are then regenerated to plants and backcrossed to the original parent plant. It can be demonstrated that the plants derived from this cross contain the desired translocation but otherwise are isogenic with the backcross parent. Thus, this method can be applied to generate lines containing targeted translocations and which are otherwise also isogenic to one of the parental lines without the need for an extensive backcrossing program.

The invention claimed is:

1. A method for removing genetic linkage between a first locus A and a second locus B present on a first plant chromosome in a plant or plant cell, the method comprising:
   (a) providing at least one plant cell comprising:
      (i) the first chromosome comprising an introgression comprising the first locus A and the second locus B, wherein the first locus A and the second locus B exhibit linkage drag with one another; and
      (ii) at least a second chromosome, wherein the chromosomes are homologous or homeologous chromosomes of each other;
   (b) introducing a double strand break at a target sequence in the first chromosome, wherein the double strand break in the first chromosome is introduced between the first locus A and the second locus B thereby providing a first part of the first chromosome comprising the first locus A and a second part of the first chromosome comprising the second locus B;
   (c) introducing a double strand break at a corresponding locus or location in the second chromosome, thereby providing a first part of the second chromosome and a second part of the second chromosome, wherein the double strand break in the first chromosome and the double strand break in the second chromosome are introduced at the same or corresponding genomic position on both of the homologous or homeologous chromosomes; and
   (d) identifying, using the at least one plant cell obtained under step (c), at least one plant cell wherein the genetic linkage between the first locus A and the second locus B on the first chromosome has been removed, and further, wherein the first part of the first chromosome comprising the first locus A is ligated to the second part of the second chromosome,
   wherein the double strand break in the first chromosome and the double strand break in the second chromosome is introduced by at least one site-specific nuclease; and wherein the at least one site-specific nuclease is a zinc finger nuclease, a meganuclease, a TAL-effector nuclease or a nuclease of CRISPR system introduced into the at least one plant cell of step (a).

2. The method of claim 1, wherein in step (d), the second part of the first chromosome is ligated to the first part of the second chromosome.

3. The method of claim 1, wherein the second chromosome does not comprise a locus that is identical to the first locus A and/or does not comprise a locus that is identical to the second locus B.

4. The method of claim 1, wherein the double strand break in the first chromosome and the double strand break in the second chromosome is introduced by the same site-specific nuclease.

5. The method of claim 1, wherein no more than one double strand break is introduced in the first chromosome and no more than one double strand break is introduced in the second chromosome.

6. The method of claim 1, wherein:
   (i) the first chromosome comprises the first locus A and the second locus B, wherein the first locus A is linked to a desirable trait of a first character and the second locus B is linked to a undesirable trait of the first character or a second character;
   (ii) wherein the second chromosome does not comprise a locus that is identical to the second locus B linked to a undesirable trait of the first character or a second character, and/or;
   (iii) one double strand break is introduced between the first locus A and the second locus B on the first chromosome and at a corresponding locus or location at the second chromosome.

7. The method of claim 6, wherein the first or second character is selected from the group consisting of yield, resistance to disease or pests, growth, size, amount of seeds, or resistance against salt, heat, cold, water or drought stress.

8. The method of claim 1, further comprising:
   (e) regenerating a plant from a plant cell obtained after step (b) of claim 1;
   (f) generating seed from the regenerated plant by selfing or crossing with another plant;
   (g) growing a plant from seed obtained in step (f), and;
   (h) optionally, screening the plant obtained in step (g) for removal of genetic linkage.

9. The method of claim 1, wherein the provided plant cell is a somatic plant cell.

10. The method of claim 9, wherein the somatic plant cell is selected from the group consisting of a protoplast, and/or a plant cell obtained from a hybrid.

11. The method of claim 1, wherein the plant is a diploid, triploid, tetraploid, pentaploid, hexaploid, octaploid, decaploid, dodecaploid or a amphidiploid.

12. A method for providing a plant P1 obtained from a plant P2, wherein the plant P2 is characterized by the presence of genetic linkage between a first locus A and a second locus B on a first chromosome, and wherein the plant P1 is characterized by the absence of the genetic linkage, the method comprising:
   (a) providing at least one plant cell from the plant P2 comprising the first chromosome comprising an introgression comprising the first locus A and the second locus B and further comprising at least a second chromosome, wherein the first locus A and the second locus B exhibit linkage drag with one another, and wherein the chromosomes are homologous or homeologous chromosomes of each other;
   (b) introducing a double strand break at an target sequence in the first chromosome, wherein the double strand break in the first chromosome is introduced between the first locus A and the second locus B, thereby providing a first part of the first chromosome comprising the first locus A and a second part of the first chromosome comprising the second locus B;
   (c) introducing a double strand break at a corresponding locus or location in the second chromosome, thereby providing a first part of the second chromosome and a second part of the second chromosome, wherein the double strand break in the first chromosome and the double strand break in the second chromosome are introduced at the same or corresponding genomic position on both of the homologous or homeologous chromosomes;
   (d) identifying, using the at least one plant cell obtained under step (c), at least one plant cell wherein the genetic linkage between the first locus A and the second locus B on the first chromosome has been removed, and further, wherein the first part of the first chromosome comprising the first locus A is ligated to the second part of the second chromosome; and
   (e) regenerating the plant P1 from the at least one plant cell identified in (d);
   wherein the double strand break in the first chromosome and the double strand break in the second chromosome is introduced by at least one site-specific nuclease, and wherein the at least one site-specific nuclease is a zinc finger nuclease, a meganuclease, a TAL-effector nuclease or a nuclease of CRISPR system introduced into the at least one plant cell of step (a).

* * * * *

SEQUENCE LISTING

```
<160> NUMBER OF SEQ ID NOS: 35

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      primer ALS2

<400> SEQUENCE: 1
tgggaatggt ggttcagtgg gagga                                            25
```

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: Synthetic
      primer ALS2

<400> SEQUENCE: 2
ggtggttcag tgggaggatc gattct                                        26

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      primer ALS2

<400> SEQUENCE: 3
cgtagctccc ggaccagatg tagca                                         25

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: Synthetic
      primer ALS2

<400> SEQUENCE: 4
atgtagcaat acaaacacca gggaaccca                                     29

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      additional primer

<400> SEQUENCE: 5
tcaccccttc accttacc                                                 18

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      additional primer 2

<400> SEQUENCE: 6
ccttcacatt taaccaaagc                                               20

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer ALS2

<400> SEQUENCE: 7
gaaagggaag gggttaagg                                                19

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      primer ALS2

<400> SEQUENCE: 8
cttcagtaga gcccttgc                                                 18

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      primer pcr

<400> SEQUENCE: 9
cttgtggagg cacttgaa                                                 18

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ccggaccaga tgtagcaata                                               20

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cttccaccct tcttcccaaa tc                                            22

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tgccaactcc tgcacattca                                               20

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Leu Ala Gly Leu Ile Asp Ala Asp Gly
1               5

<210> SEQ ID NO 14
<211> LENGTH: 2984
<212> TYPE: DNA
<213> ORGANISM: Solanum pennellii

<400> SEQUENCE: 14

| | | | | | | |
|---|---|---|---|---|---|---|
| cctcaacaac | aatggcggct | gcatctccat | ctccttgttt | ttccaaaacc | ctacctccat | 60 |
| cttcatcaaa | atcttccacc | cttcttccca | aatctacctt | tactttccac | aatcacccta | 120 |
| aaaaagcatc | accccttcac | cttacacaca | cccaacatca | tagccgtttc | actgtttcaa | 180 |
| atgtcatcct | atcaaccacg | acgcatgacg | acgtttctga | acccgaaatc | tttgtttccc | 240 |
| gtttcgcccc | tgacgaaccc | agaaagggtt | gtgatgttct | tgtggaggca | cttgaaaggg | 300 |
| aaggggttaa | ggatgtgttt | gcatacccag | gaggtgcttc | catggagatt | catcaggctt | 360 |
| tgacacgttc | aaatattatt | cgtaatgtgc | tgccacgtca | tgaacagggt | ggtgtgtttg | 420 |
| ctgcagaggg | ttacgcacgg | gctactgggt | ccctggtgt | ttgtattgct | acatctggtc | 480 |
| cgggagctac | gaatcttgtt | agcggtcttg | ctgatgcttt | gttggatagt | atcccgattg | 540 |
| ttgctattac | cggtcaagtg | ccgaggagga | tgattggtac | tgatgcgttt | caggaaactc | 600 |
| ctattgttga | ggtaacgaga | tccattacga | agcataatta | tcttgttatg | gatgtagagg | 660 |
| atattcctag | ggttgttcgt | gaagcgtttt | ttctagcgaa | atcaggacgg | cctggacctg | 720 |
| ttttgattga | tgttcctaag | gatattcagc | aacaattggt | gataccctaat | tgggatcagc | 780 |
| caatgaggtt | gcctggttac | atgtctaggt | tgcctaaatt | acctaatgag | atgcttttgg | 840 |
| aacaaattgt | taggctgatt | tcagagtcaa | agaagcctgt | tttgtatgtg | ggtggtgggt | 900 |
| gttcacagtc | gagtgaggag | ctgagacgct | tgtggagct | tacgggtatt | cctgtggcga | 960 |
| gtactttgat | gggtcttgga | gcttttccaa | gtggggatga | gctttctctt | caaatgttgg | 1020 |
| gtatgcatgg | gactgtgtat | gctaattatg | cggtggatag | tagtgatttg | ttgcttgcat | 1080 |
| ttggggtgag | gtttgatgat | cgagttactg | gtaaattgga | agcttttgct | agccgagcta | 1140 |
| agattgtcca | tattgatatt | gattcggctg | agattggaaa | gaacaagcaa | cctcatgttt | 1200 |
| ccatctgtgc | agatatcaag | ttggcattac | agggtttgaa | ttccatattc | gagagtaaaa | 1260 |
| aaggtaagct | gaagttggac | ttttctgctt | ggaggcagga | gttaacggag | cagaaggtga | 1320 |
| agtaccatt | gaattttaag | actttcggtg | aagccatccc | tccccaatat | gctattcagg | 1380 |
| ttcttgatga | gttaactaac | ggaaatgcca | tcattagtac | tggtgtgggg | caacaccaaa | 1440 |
| tgtgggctgc | ccaacactac | aagtacaaaa | agccacgcca | atggcttaca | tctggtggat | 1500 |
| taggagcaat | gggatttggt | ttgcctgctg | ctataggtgc | ggctgttgga | agaccgggtg | 1560 |
| agattgtggt | tgatattgat | ggtgatggga | gttttatcat | gaatgtgcag | gagttggcaa | 1620 |
| caattaaggt | ggagaatctc | ccagttaaga | ttatgttgct | gaataatcaa | cacttgggaa | 1680 |
| tggtggttca | gtgggaggat | cgattctata | aggctaacag | agcacacact | tacttgggta | 1740 |
| atcctgctaa | tgaggaagag | atcttcccta | atatgctgaa | atttgcagag | gcttgtggcg | 1800 |
| tacctgctgc | aagagtgtca | cacagggatg | atcttagagc | tgccattcaa | aagatgttag | 1860 |
| acactcctgg | gccatacttg | ttggatgtga | ttgtacctca | tcaggagcat | gttctaccga | 1920 |
| tgattcccag | tggcggtgct | ttcaaagatg | tgattacgga | gggtgatggg | agacgttcct | 1980 |
| attgactttg | agaagctaca | taactagttc | aaggcattgt | attatctaaa | ataaacttaa | 2040 |
| tatttatgtt | tacttaaaag | ttttcattg | tgtgaaggat | tttagaattt | cttgttctat | 2100 |
| tggcagcacc | aattaagtat | ttggagctct | atttagtatg | actaagatta | attacaagtg | 2160 |

-continued

```
aagtagttaa gttcgataaa tcagctttgt tacattctat gttatttggt gaacatgaat    2220
tccatttggg agaaggctat gtccagctta agggctcaaa ttttcagag agtgctgatt     2280 caaaaggtga atgccaaaat cagattagca caagtttgca gagttatatt acgccatctt    2340
tctgttttca gctaattgct gttgcaaggg ctctactgaa gaaggcctct attttatttc    2400
ttgatgaggt aatctttgac ccctttgct ccccgtgtgt ccgttgactt ttaccatgta     2460
tgctctgcgt tacagttctg tgggtgacct tggtatcttc ttattcactg taaatgttgg    2520
tttaagcctg aattacctag gggattcccc aggtcgttta cacaggggtt tacataagat    2580
cagctcagtt ctccggagaa gttctagcaa tcttggagag cctatttcat ctctgcatgt    2640
gaatcttagg gcagttaatg ccaaggatat cagagtgaag attatagtgg atgacaccat    2700
tttgccttca tcattagcaa caacacctac agaagatgga aaagagaacg gtgcaggaaa    2760
tgggaaaagt ttcacaaatg gggcaagacg aagagaatcc ttaaagatgc tggcaaatct    2820
gttggtggtg gcataaagga agtgatgtct gggaagtcat cagggaaatc taaagaggaa    2880
gtagaatcat cagagaccga agaatgagc tctgtggaat ctgatatttc tgatgcagag     2940
tctcaacctt catcagttga ttcacctcca gttgtagcgc cttc                     2984
```

<210> SEQ ID NO 15
<211> LENGTH: 38
<212> TYPE: DNA
<213> ORGANISM: Solanum pennellii

<400> SEQUENCE: 15
aatgtgctgc cacgtcatga acagggtggt gtgtttgc                            38

<210> SEQ ID NO 16
<211> LENGTH: 35
<212> TYPE: DNA
<213> ORGANISM: Solanum pennellii

<400> SEQUENCE: 16
aatgtgctgc cacgtcaaca gggtggtgtg tttgc                               35

<210> SEQ ID NO 17
<211> LENGTH: 34
<212> TYPE: DNA
<213> ORGANISM: Solanum pennellii

<400> SEQUENCE: 17
aatgtgctgc cacgtcacag ggtggtgtgt ttgc                                34

<210> SEQ ID NO 18
<211> LENGTH: 37
<212> TYPE: DNA
<213> ORGANISM: Solanum pennellii

<400> SEQUENCE: 18
aatgtgctgc cacgtcagaa cagggtggtg tgtttgc                             37

<210> SEQ ID NO 19
<211> LENGTH: 35
<212> TYPE: DNA
<213> ORGANISM: Solanum pennellii

<400> SEQUENCE: 19
aatgtgctgc cacgtcatga gggtggtgtg tttgc                               35

<210> SEQ ID NO 20
<211> LENGTH: 31
<212> TYPE: DNA
<213> ORGANISM: Solanum pennellii

<400> SEQUENCE: 20
aatgtgctgc cacgtcgggt ggtgtgtttg c    31

<210> SEQ ID NO 21
<211> LENGTH: 32
<212> TYPE: DNA
<213> ORGANISM: Solanum pennellii

<400> SEQUENCE: 21
aatgtgctgc cacgtcaggg tggtgtgttt gc    32

<210> SEQ ID NO 22
<211> LENGTH: 35
<212> TYPE: DNA
<213> ORGANISM: Solanum pennellii

<400> SEQUENCE: 22
aatgtgctgc cacgtcaaca gggtggtgtg tttgc    35

<210> SEQ ID NO 23
<211> LENGTH: 516
<212> TYPE: DNA
<213> ORGANISM: Solanum pennellii
<220> FEATURE:
<221> NAME/KEY: modified_base
<222> LOCATION: (65)..(510)
<223> OTHER INFORMATION: a, c, t, g, unknown or other

<400> SEQUENCE: 23
catcaggctt tgacacgttc aaatattatt cgtaatgtgc tgccacgtca tgaacagggt    60
ggtgnnnnnn nnnnnnnnnn nnnnnnnnnn nnnnnnnnnn nnnnnnnnnn nnnnnnnnnn   120
nnnnnnnnnn nnnnnnnnnn nnnnnnnnnn nnnnnnnnnn nnnnnnnnnn nnnnnnnnnn   180
nnnnnnnnnn nnnnnnnnnn nnnnnnnnnn nnnnnnnnnn nnnnnnnnnn nnnnnnnnnn   240
nnnnnnnnnn nnnnnnnnnn nnnnnnnnnn nnnnnnnnnn nnnnnnnnnn nnnnnnnnnn   300
nnnnnnnnnn nnnnnnnnnn nnnnnnnnnn nnnnnnnnnn nnnnnnnnnn nnnnnnnnnn   360
nnnnnnnnnn nnnnnnnnnn nnnnnnnnnn nnnnnnnnnn nnnnnnnnnn nnnnnnnnnn   420
nnnnnnnnnn nnnnnnnnnn nnnnnnnnnn nnnnnnnnnn nnnnnnnnnn nnnnnnnnnn   480
nnnnnnnnnn nnnnnnnnnn nnnnnnnnnn tcagag                             516

<210> SEQ ID NO 24
<211> LENGTH: 516
<212> TYPE: DNA
<213> ORGANISM: Solanum pennellii
<220> FEATURE:
<221> NAME/KEY: modified_base
<222> LOCATION: (65)..(510)
<223> OTHER INFORMATION: a, c, t, g, unknown or other

<400> SEQUENCE: 24
catcaagctt tgacacgttc gaatattatt cgtaatgtgc tgccacgtca tgaacagggt    60
ggtgnnnnnn nnnnnnnnnn nnnnnnnnnn nnnnnnnnnn nnnnnnnnnn nnnnnnnnnn   120
nnnnnnnnnn nnnnnnnnnn nnnnnnnnnn nnnnnnnnnn nnnnnnnnnn nnnnnnnnnn   180
nnnnnnnnnn nnnnnnnnnn nnnnnnnnnn nnnnnnnnnn nnnnnnnnnn nnnnnnnnnn   240

```
nnnnnnnnnn nnnnnnnnnn nnnnnnnnnn nnnnnnnnnn nnnnnnnnnn nnnnnnnnnn    300
nnnnnnnnnn nnnnnnnnnn nnnnnnnnnn nnnnnnnnnn nnnnnnnnnn nnnnnnnnnn    360
nnnnnnnnnn nnnnnnnnnn nnnnnnnnnn nnnnnnnnnn nnnnnnnnnn nnnnnnnnnn    420
nnnnnnnnnn nnnnnnnnnn nnnnnnnnnn nnnnnnnnnn nnnnnnnnnn nnnnnnnnnn    480
nnnnnnnnnn nnnnnnnnnn nnnnnnnnnn tcggag                              516
```

<210> SEQ ID NO 25
<211> LENGTH: 516
<212> TYPE: DNA
<213> ORGANISM: Solanum pennellii
<220> FEATURE:
<221> NAME/KEY: modified_base
<222> LOCATION: (65)..(510)
<223> OTHER INFORMATION: a, c, t, g, unknown or other

<400> SEQUENCE: 25

```
catcaggctt tgacacgttc aaatattatt cgtaatgtgc tgccacgtca tgaacagggt     60
ggtgnnnnnn nnnnnnnnnn nnnnnnnnnn nnnnnnnnnn nnnnnnnnnn nnnnnnnnnn    120
nnnnnnnnnn nnnnnnnnnn nnnnnnnnnn nnnnnnnnnn nnnnnnnnnn nnnnnnnnnn    180
nnnnnnnnnn nnnnnnnnnn nnnnnnnnnn nnnnnnnnnn nnnnnnnnnn nnnnnnnnnn    240
nnnnnnnnnn nnnnnnnnnn nnnnnnnnnn nnnnnnnnnn nnnnnnnnnn nnnnnnnnnn    300
nnnnnnnnnn nnnnnnnnnn nnnnnnnnnn nnnnnnnnnn nnnnnnnnnn nnnnnnnnnn    360
nnnnnnnnnn nnnnnnnnnn nnnnnnnnnn nnnnnnnnnn nnnnnnnnnn nnnnnnnnnn    420
nnnnnnnnnn nnnnnnnnnn nnnnnnnnnn nnnnnnnnnn nnnnnnnnnn nnnnnnnnnn    480
nnnnnnnnnn nnnnnnnnnn nnnnnnnnnn tcagag                              516
```

<210> SEQ ID NO 26
<211> LENGTH: 516
<212> TYPE: DNA
<213> ORGANISM: Solanum pennellii
<220> FEATURE:
<221> NAME/KEY: modified_base
<222> LOCATION: (65)..(510)
<223> OTHER INFORMATION: a, c, t, g, unknown or other

<400> SEQUENCE: 26

```
catcaagctt tgacacgttc gaatattatt cgtaatgtgc tgccacgtca tgaacagggt     60
ggtgnnnnnn nnnnnnnnnn nnnnnnnnnn nnnnnnnnnn nnnnnnnnnn nnnnnnnnnn    120
nnnnnnnnnn nnnnnnnnnn nnnnnnnnnn nnnnnnnnnn nnnnnnnnnn nnnnnnnnnn    180
nnnnnnnnnn nnnnnnnnnn nnnnnnnnnn nnnnnnnnnn nnnnnnnnnn nnnnnnnnnn    240
nnnnnnnnnn nnnnnnnnnn nnnnnnnnnn nnnnnnnnnn nnnnnnnnnn nnnnnnnnnn    300
nnnnnnnnnn nnnnnnnnnn nnnnnnnnnn nnnnnnnnnn nnnnnnnnnn nnnnnnnnnn    360
nnnnnnnnnn nnnnnnnnnn nnnnnnnnnn nnnnnnnnnn nnnnnnnnnn nnnnnnnnnn    420
nnnnnnnnnn nnnnnnnnnn nnnnnnnnnn nnnnnnnnnn nnnnnnnnnn nnnnnnnnnn    480
nnnnnnnnnn nnnnnnnnnn nnnnnnnnnn tcggag                              516
```

<210> SEQ ID NO 27
<211> LENGTH: 516
<212> TYPE: DNA
<213> ORGANISM: Solanum pennellii
<220> FEATURE:
<221> NAME/KEY: modified_base
<222> LOCATION: (65)..(510)

<223> OTHER INFORMATION: a, c, t, g, unknown or other

<400> SEQUENCE: 27

| | |
|---|---|
| catcaggctt tgacacgttc aaatattatt cgtaatgtgc tgccacgtca tgaacagggt | 60 |
| ggtgnnnnnn nnnnnnnnnn nnnnnnnnnn nnnnnnnnnn nnnnnnnnnn nnnnnnnnnn | 120 |
| nnnnnnnnnn nnnnnnnnnn nnnnnnnnnn nnnnnnnnnn nnnnnnnnnn nnnnnnnnnn | 180 |
| nnnnnnnnnn nnnnnnnnnn nnnnnnnnnn nnnnnnnnnn nnnnnnnnnn nnnnnnnnnn | 240 |
| nnnnnnnnnn nnnnnnnnnn nnnnnnnnnn nnnnnnnnnn nnnnnnnnnn nnnnnnnnnn | 300 |
| nnnnnnnnnn nnnnnnnnnn nnnnnnnnnn nnnnnnnnnn nnnnnnnnnn nnnnnnnnnn | 360 |
| nnnnnnnnnn nnnnnnnnnn nnnnnnnnnn nnnnnnnnnn nnnnnnnnnn nnnnnnnnnn | 420 |
| nnnnnnnnnn nnnnnnnnnn nnnnnnnnnn nnnnnnnnnn nnnnnnnnnn nnnnnnnnnn | 480 |
| nnnnnnnnnn nnnnnnnnnn nnnnnnnnnn tcagag | 516 |

<210> SEQ ID NO 28
<211> LENGTH: 516
<212> TYPE: DNA
<213> ORGANISM: Solanum pennellii
<220> FEATURE:
<221> NAME/KEY: modified_base
<222> LOCATION: (65)..(510)
<223> OTHER INFORMATION: a, c, t, g, unknown or other

<400> SEQUENCE: 28

| | |
|---|---|
| catcaagctt tgacacgttc gaatattatt cgtaatgtgc tgccacgtca tgaacagggt | 60 |
| ggtgnnnnnn nnnnnnnnnn nnnnnnnnnn nnnnnnnnnn nnnnnnnnnn nnnnnnnnnn | 120 |
| nnnnnnnnnn nnnnnnnnnn nnnnnnnnnn nnnnnnnnnn nnnnnnnnnn nnnnnnnnnn | 180 |
| nnnnnnnnnn nnnnnnnnnn nnnnnnnnnn nnnnnnnnnn nnnnnnnnnn nnnnnnnnnn | 240 |
| nnnnnnnnnn nnnnnnnnnn nnnnnnnnnn nnnnnnnnnn nnnnnnnnnn nnnnnnnnnn | 300 |
| nnnnnnnnnn nnnnnnnnnn nnnnnnnnnn nnnnnnnnnn nnnnnnnnnn nnnnnnnnnn | 360 |
| nnnnnnnnnn nnnnnnnnnn nnnnnnnnnn nnnnnnnnnn nnnnnnnnnn nnnnnnnnnn | 420 |
| nnnnnnnnnn nnnnnnnnnn nnnnnnnnnn nnnnnnnnnn nnnnnnnnnn nnnnnnnnnn | 480 |
| nnnnnnnnnn nnnnnnnnnn nnnnnnnnnn tcggag | 516 |

<210> SEQ ID NO 29
<211> LENGTH: 510
<212> TYPE: DNA
<213> ORGANISM: Solanum pennellii
<220> FEATURE:
<221> NAME/KEY: modified_base
<222> LOCATION: (59)..(504)
<223> OTHER INFORMATION: a, c, t, g, unknown or other

<400> SEQUENCE: 29

| | |
|---|---|
| catcaagctt tgacacgttc gaatattatt cgtaatgtgc tgccacgtca gggtggtgnn | 60 |
| nnnnnnnnnn nnnnnnnnnn nnnnnnnnnn nnnnnnnnnn nnnnnnnnnn nnnnnnnnnn | 120 |
| nnnnnnnnnn nnnnnnnnnn nnnnnnnnnn nnnnnnnnnn nnnnnnnnnn nnnnnnnnnn | 180 |
| nnnnnnnnnn nnnnnnnnnn nnnnnnnnnn nnnnnnnnnn nnnnnnnnnn nnnnnnnnnn | 240 |
| nnnnnnnnnn nnnnnnnnnn nnnnnnnnnn nnnnnnnnnn nnnnnnnnnn nnnnnnnnnn | 300 |
| nnnnnnnnnn nnnnnnnnnn nnnnnnnnnn nnnnnnnnnn nnnnnnnnnn nnnnnnnnnn | 360 |
| nnnnnnnnnn nnnnnnnnnn nnnnnnnnnn nnnnnnnnnn nnnnnnnnnn nnnnnnnnnn | 420 |
| nnnnnnnnnn nnnnnnnnnn nnnnnnnnnn nnnnnnnnnn nnnnnnnnnn nnnnnnnnnn | 480 |

```
nnnnnnnnnn nnnnnnnnnn nnnntcagag                                   510
```

<210> SEQ ID NO 30
<211> LENGTH: 509
<212> TYPE: DNA
<213> ORGANISM: Solanum pennellii
<220> FEATURE:
<221> NAME/KEY: modified_base
<222> LOCATION: (58)..(503)
<223> OTHER INFORMATION: a, c, t, g, unknown or other

<400> SEQUENCE: 30

```
catcaagctt tgacacgttc gaatattatt cgtaatgtgc tgccacgtca ggtggtgnnn    60
nnnnnnnnnn nnnnnnnnnn nnnnnnnnnn nnnnnnnnnn nnnnnnnnnn nnnnnnnnnn   120
nnnnnnnnnn nnnnnnnnnn nnnnnnnnnn nnnnnnnnnn nnnnnnnnnn nnnnnnnnnn   180
nnnnnnnnnn nnnnnnnnnn nnnnnnnnnn nnnnnnnnnn nnnnnnnnnn nnnnnnnnnn   240
nnnnnnnnnn nnnnnnnnnn nnnnnnnnnn nnnnnnnnnn nnnnnnnnnn nnnnnnnnnn   300
nnnnnnnnnn nnnnnnnnnn nnnnnnnnnn nnnnnnnnnn nnnnnnnnnn nnnnnnnnnn   360
nnnnnnnnnn nnnnnnnnnn nnnnnnnnnn nnnnnnnnnn nnnnnnnnnn nnnnnnnnnn   420
nnnnnnnnnn nnnnnnnnnn nnnnnnnnnn nnnnnnnnnn nnnnnnnnnn nnnnnnnnnn   480
nnnnnnnnnn nnnnnnnnnn nnntcagag                                    509
```

<210> SEQ ID NO 31
<211> LENGTH: 510
<212> TYPE: DNA
<213> ORGANISM: Solanum pennellii
<220> FEATURE:
<221> NAME/KEY: modified_base
<222> LOCATION: (59)..(504)
<223> OTHER INFORMATION: a, c, t, g, unknown or other

<400> SEQUENCE: 31

```
catcaagctt tgacacgttc gaatattatt cgtaatgtgc tgccacgtca gggtggtgnn    60
nnnnnnnnnn nnnnnnnnnn nnnnnnnnnn nnnnnnnnnn nnnnnnnnnn nnnnnnnnnn   120
nnnnnnnnnn nnnnnnnnnn nnnnnnnnnn nnnnnnnnnn nnnnnnnnnn nnnnnnnnnn   180
nnnnnnnnnn nnnnnnnnnn nnnnnnnnnn nnnnnnnnnn nnnnnnnnnn nnnnnnnnnn   240
nnnnnnnnnn nnnnnnnnnn nnnnnnnnnn nnnnnnnnnn nnnnnnnnnn nnnnnnnnnn   300
nnnnnnnnnn nnnnnnnnnn nnnnnnnnnn nnnnnnnnnn nnnnnnnnnn nnnnnnnnnn   360
nnnnnnnnnn nnnnnnnnnn nnnnnnnnnn nnnnnnnnnn nnnnnnnnnn nnnnnnnnnn   420
nnnnnnnnnn nnnnnnnnnn nnnnnnnnnn nnnnnnnnnn nnnnnnnnnn nnnnnnnnnn   480
nnnnnnnnnn nnnnnnnnnn nnnntcagag                                   510
```

<210> SEQ ID NO 32
<211> LENGTH: 513
<212> TYPE: DNA
<213> ORGANISM: Solanum pennellii
<220> FEATURE:
<221> NAME/KEY: modified_base
<222> LOCATION: (62)..(507)
<223> OTHER INFORMATION: a, c, t, g, unknown or other

<400> SEQUENCE: 32

```
catcaagctt tgacacgttc gaatattatt cgtaatgtgc tgccacgtca acagggtggt    60
gnnnnnnnnn nnnnnnnnnn nnnnnnnnnn nnnnnnnnnn nnnnnnnnnn nnnnnnnnnn   120
```

-continued

| | |
|---|---|
| nnnnnnnnnn nnnnnnnnnn nnnnnnnnnn nnnnnnnnnn nnnnnnnnnn nnnnnnnnnn | 180 |
| nnnnnnnnnn nnnnnnnnnn nnnnnnnnnn nnnnnnnnnn nnnnnnnnnn nnnnnnnnnn | 240 |
| nnnnnnnnnn nnnnnnnnnn nnnnnnnnnn nnnnnnnnnn nnnnnnnnnn nnnnnnnnnn | 300 |
| nnnnnnnnnn nnnnnnnnnn nnnnnnnnnn nnnnnnnnnn nnnnnnnnnn nnnnnnnnnn | 360 |
| nnnnnnnnnn nnnnnnnnnn nnnnnnnnnn nnnnnnnnnn nnnnnnnnnn nnnnnnnnnn | 420 |
| nnnnnnnnnn nnnnnnnnnn nnnnnnnnnn nnnnnnnnnn nnnnnnnnnn nnnnnnnnnn | 480 |
| nnnnnnnnnn nnnnnnnnnn nnnnnnntca gag | 513 |

```
<210> SEQ ID NO 33
<211> LENGTH: 512
<212> TYPE: DNA
<213> ORGANISM: Solanum pennellii
<220> FEATURE:
<221> NAME/KEY: modified_base
<222> LOCATION: (61)..(506)
<223> OTHER INFORMATION: a, c, t, g, unknown or other

<400> SEQUENCE: 33
```

| | |
|---|---|
| catcaagctt tgacacgttc gaatattatt cgtaatgtgc tgccacgtca cagggtggtg | 60 |
| nnnnnnnnnn nnnnnnnnnn nnnnnnnnnn nnnnnnnnnn nnnnnnnnnn nnnnnnnnnn | 120 |
| nnnnnnnnnn nnnnnnnnnn nnnnnnnnnn nnnnnnnnnn nnnnnnnnnn nnnnnnnnnn | 180 |
| nnnnnnnnnn nnnnnnnnnn nnnnnnnnnn nnnnnnnnnn nnnnnnnnnn nnnnnnnnnn | 240 |
| nnnnnnnnnn nnnnnnnnnn nnnnnnnnnn nnnnnnnnnn nnnnnnnnnn nnnnnnnnnn | 300 |
| nnnnnnnnnn nnnnnnnnnn nnnnnnnnnn nnnnnnnnnn nnnnnnnnnn nnnnnnnnnn | 360 |
| nnnnnnnnnn nnnnnnnnnn nnnnnnnnnn nnnnnnnnnn nnnnnnnnnn nnnnnnnnnn | 420 |
| nnnnnnnnnn nnnnnnnnnn nnnnnnnnnn nnnnnnnnnn nnnnnnnnnn nnnnnnnnnn | 480 |
| nnnnnnnnnn nnnnnnnnnn nnnnnntcag ag | 512 |

```
<210> SEQ ID NO 34
<211> LENGTH: 511
<212> TYPE: DNA
<213> ORGANISM: Solanum pennellii
<220> FEATURE:
<221> NAME/KEY: modified_base
<222> LOCATION: (60)..(505)
<223> OTHER INFORMATION: a, c, t, g, unknown or other

<400> SEQUENCE: 34
```

| | |
|---|---|
| catcaagctt tgacacgttc gaatattatt cgtaatgtgc tgccacgtca agggtggtgn | 60 |
| nnnnnnnnnn nnnnnnnnnn nnnnnnnnnn nnnnnnnnnn nnnnnnnnnn nnnnnnnnnn | 120 |
| nnnnnnnnnn nnnnnnnnnn nnnnnnnnnn nnnnnnnnnn nnnnnnnnnn nnnnnnnnnn | 180 |
| nnnnnnnnnn nnnnnnnnnn nnnnnnnnnn nnnnnnnnnn nnnnnnnnnn nnnnnnnnnn | 240 |
| nnnnnnnnnn nnnnnnnnnn nnnnnnnnnn nnnnnnnnnn nnnnnnnnnn nnnnnnnnnn | 300 |
| nnnnnnnnnn nnnnnnnnnn nnnnnnnnnn nnnnnnnnnn nnnnnnnnnn nnnnnnnnnn | 360 |
| nnnnnnnnnn nnnnnnnnnn nnnnnnnnnn nnnnnnnnnn nnnnnnnnnn nnnnnnnnnn | 420 |
| nnnnnnnnnn nnnnnnnnnn nnnnnnnnnn nnnnnnnnnn nnnnnnnnnn nnnnnnnnnn | 480 |
| nnnnnnnnnn nnnnnnnnnn nnnnntcaga g | 511 |

```
<210> SEQ ID NO 35
<211> LENGTH: 513
<212> TYPE: DNA
<213> ORGANISM: Solanum pennellii
```

```
-continued

<220> FEATURE:
<221> NAME/KEY: modified_base
<222> LOCATION: (62)..(507)
<223> OTHER INFORMATION: a, c, t, g, unknown or other

<400> SEQUENCE: 35
catcaggctt tgacacgttc aaatattatt cgtaatgtgc tgccacgtca tcagggtggt      60
gnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn nnnnnnnnnn nnnnnnnnnn nnnnnnnnnn nnnnnnnnnn nnnnnnnnnn     360
nnnnnnnnnn nnnnnnnnnn nnnnnnnnnn nnnnnnnnnn nnnnnnnnnn nnnnnnnnnn     420
nnnnnnnnnn nnnnnnnnnn nnnnnnnnnn nnnnnnnnnn nnnnnnnnnn nnnnnnnnnn     480
nnnnnnnnnn nnnnnnnnnn nnnnnnntcg gag                                  513
```

UNITED STATES PATENT AND TRADEMARK OFFICE
CERTIFICATE OF CORRECTION

| | | |
|---|---|---|
| PATENT NO. | : 10,995,338 B2 | |
| APPLICATION NO. | : 14/655633 | |
| DATED | : May 4, 2021 | |
| INVENTOR(S) | : Bundock et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 373 days.

Signed and Sealed this
Sixth Day of December, 2022

Katherine Kelly Vidal
*Director of the United States Patent and Trademark Office*